US009901616B2

(12) United States Patent
Dhar et al.

(10) Patent No.: US 9,901,616 B2
(45) Date of Patent: Feb. 27, 2018

(54) APOPTOSIS-TARGETING NANOPARTICLES

(75) Inventors: Shanta Dhar, Miami, FL (US); Sean Marrache, Portland, OR (US)

(73) Assignee: UNIVERSITY OF GEORGIA RESEARCH FOUNDATION, INC., Athens, GA (US)

(*) Notice: Subject to any disclaimer, the term of this patent is extended or adjusted under 35 U.S.C. 154(b) by 0 days.

(21) Appl. No.: 14/240,081

(22) PCT Filed: Aug. 31, 2012

(86) PCT No.: PCT/US2012/053307
§ 371 (c)(1),
(2), (4) Date: May 22, 2014

(87) PCT Pub. No.: WO2013/033513
PCT Pub. Date: Mar. 7, 2013

(65) Prior Publication Data
US 2014/0303081 A1 Oct. 9, 2014

Related U.S. Application Data

(60) Provisional application No. 61/529,637, filed on Aug. 31, 2011.

(51) Int. Cl.
| A61K 38/17 | (2006.01) |
| A61K 49/00 | (2006.01) |
| A61K 49/18 | (2006.01) |
| A61K 31/315 | (2006.01) |
| A61K 38/08 | (2006.01) |
| A61K 45/06 | (2006.01) |
| A61K 47/54 | (2017.01) |
| A61K 47/69 | (2017.01) |

(52) U.S. Cl.
CPC ........ *A61K 38/1709* (2013.01); *A61K 31/315* (2013.01); *A61K 38/08* (2013.01); *A61K 45/06* (2013.01); *A61K 47/54* (2017.08); *A61K 47/549* (2017.08); *A61K 47/6921* (2017.08); *A61K 47/6935* (2017.08); *A61K 47/6937* (2017.08); *A61K 49/0067* (2013.01); *A61K 49/0093* (2013.01); *A61K 49/1881* (2013.01)

(58) Field of Classification Search
CPC ........ A61K 47/48023; A61K 47/48092; A61K 47/48907; A61K 47/48915; A61K 49/0067; A61K 49/0093; A61K 49/1881; A61K 31/315; A61K 38/08; A61K 38/1709; A61K 45/06; A61K 47/48853
See application file for complete search history.

(56) References Cited

U.S. PATENT DOCUMENTS

| 4,239,757 | A |   | 12/1980 | Bodor |
| 4,999,344 | A | * | 3/1991  | Jett-Tilton ............ A61K 9/127 514/76 |
| 6,217,864 | B1 |   | 4/2001  | Coffino et al. |
| 6,753,154 | B1 |   | 6/2004  | Chen et al. |
| 6,835,718 | B2 |   | 12/2004 | Kosak |
| 7,329,638 | B2 |   | 2/2008  | Yang et al. |
| 7,393,924 | B2 |   | 7/2008  | Vitaliano et al. |
| 7,638,558 | B2 |   | 12/2009 | Breitenkamp et al. |
| 7,671,095 | B2 |   | 3/2010  | Colson et al. |
| 7,725,169 | B2 |   | 5/2010  | Boppart et al. |
| 7,728,036 | B2 |   | 6/2010  | Huang et al. |
| 7,858,843 | B2 |   | 12/2010 | Culbertson et al. |
| 7,871,596 | B2 |   | 1/2011  | Kuniyoshi et al. |
| 7,931,902 | B2 |   | 4/2011  | De Sauvage et al. |
| 7,935,782 | B2 |   | 5/2011  | Harth et al. |
| 7,947,866 | B2 |   | 5/2011  | Sparks |
| 7,956,237 | B2 |   | 6/2011  | Montgomery et al. |
| 8,067,664 | B2 |   | 11/2011 | Huang |
| 8,128,908 | B2 |   | 3/2012  | Santra et al. |
| 8,178,527 | B2 |   | 5/2012  | Chen et al. |
| 8,207,396 | B2 |   | 6/2012  | Payne et al. |
| 8,221,480 | B2 |   | 7/2012  | Boyden et al. |
| 8,227,661 | B2 |   | 7/2012  | Edwards et al. |
| 8,256,233 | B2 |   | 9/2012  | Boyden et al. |

(Continued)

FOREIGN PATENT DOCUMENTS

| EP | 1995321 A2 | 11/2008 |
| EP | 2002714 A1 | 12/2008 |
| EP | 2050335 A1 | 4/2009 |
| EP | 2082645 A1 | 7/2009 |
| EP | 1907444 B1 | 8/2009 |
| EP | 1846355 B1 | 12/2009 |
| EP | 2186402 A1 | 5/2010 |
| EP | 2248903 A1 | 11/2010 |
| EP | 2430923 A1 | 3/2012 |
| JP | 2007-526907 A | 9/2007 |
| JP | 2008/297268 A | 12/2008 |
| WO | WO 00/00503 A1 | 1/2000 |
| WO | WO 00/45838 A1 | 8/2000 |

(Continued)

OTHER PUBLICATIONS

Szeto, The AAPS Journal 2006;8(2) Article 32, E277-E283.*

(Continued)

*Primary Examiner* — Robert Cabral
(74) *Attorney, Agent, or Firm* — Mueting, Raasch & Gebhardt, P.A.

(57) ABSTRACT

Nanoparticles include a core and one or more targeting moieties, as well as one or more contrast agents or one or more therapeutic agents. The contrast agents or therapeutic agents may be contained or embedded within the core. If the nanoparticle includes therapeutic agents, the agents are preferably released from the core at a desired rate. The core may be biodegradable and may release the agents as the core is degraded or eroded. The targeting moieties preferably extend outwardly from the core so that they are available for interaction with cellular components, which interactions will target the nanoparticles to the appropriate cells, such as apoptotic cells; organelles, such as mitochondria; or the like. The targeting moieties may be tethered to the core or components that interact with the core.

10 Claims, 16 Drawing Sheets

(56) References Cited

U.S. PATENT DOCUMENTS

| | | |
|---|---|---|
| 8,263,663 B2 | 9/2012 | Sill et al. |
| 8,263,665 B2 | 9/2012 | Sill et al. |
| 8,273,373 B2 | 9/2012 | Alsberg et al. |
| 8,282,967 B2 | 10/2012 | Schoenfisch et al. |
| 8,297,959 B2 | 10/2012 | Larsen et al. |
| 8,299,128 B2 | 10/2012 | Sill et al. |
| 8,449,915 B1 | 5/2013 | Sung et al. |
| 8,574,544 B1 | 11/2013 | Sung et al. |
| 8,951,561 B2 | 2/2015 | Vo-Dinh |
| 2001/0021703 A1 | 9/2001 | Kosak |
| 2004/0038406 A1 | 2/2004 | Unger et al. |
| 2005/0025820 A1 | 2/2005 | Kester et al. |
| 2005/0042753 A1 | 2/2005 | Yang et al. |
| 2005/0153913 A1 | 7/2005 | Kosak |
| 2006/0040879 A1 | 2/2006 | Kosak |
| 2006/0228299 A1 | 10/2006 | Thorpe et al. |
| 2006/0240092 A1 | 10/2006 | Breitenkamp et al. |
| 2006/0292099 A1 | 12/2006 | Milburn et al. |
| 2007/0014833 A1 | 1/2007 | Milburn et al. |
| 2007/0066552 A1 | 3/2007 | Clarke et al. |
| 2007/0098713 A1 | 5/2007 | Unger et al. |
| 2007/0134340 A1 | 6/2007 | Prasad et al. |
| 2007/0141163 A1 | 6/2007 | Vitaliano et al. |
| 2007/0258889 A1 | 11/2007 | Douglas et al. |
| 2007/0269382 A1 | 11/2007 | Santra et al. |
| 2007/0292353 A1 | 12/2007 | Levy et al. |
| 2007/0292438 A1 | 12/2007 | Anderson et al. |
| 2007/0296099 A1 | 12/2007 | Larsen et al. |
| 2008/0018078 A1 | 1/2008 | Van Landingham, Jr. et al. |
| 2008/0051323 A1 | 2/2008 | Kosak |
| 2008/0069857 A1 | 3/2008 | Yeo et al. |
| 2008/0075718 A1 | 3/2008 | Colson et al. |
| 2008/0124344 A1 | 5/2008 | Combs et al. |
| 2008/0138277 A1* | 6/2008 | Epstein ................ G06F 1/1626 424/1.61 |
| 2008/0160034 A1 | 7/2008 | Brennan et al. |
| 2008/0187487 A1 | 8/2008 | Larsen et al. |
| 2008/0206150 A1 | 8/2008 | Louie et al. |
| 2008/0243049 A1 | 10/2008 | Hardy |
| 2008/0253961 A1 | 10/2008 | Braden et al. |
| 2008/0294089 A1 | 11/2008 | Hardy |
| 2008/0299177 A1 | 12/2008 | Hardy |
| 2008/0299182 A1 | 12/2008 | Zhang et al. |
| 2008/0305106 A1 | 12/2008 | Brennan et al. |
| 2008/0311045 A1 | 12/2008 | Hardy |
| 2008/0311107 A1 | 12/2008 | Bollinger et al. |
| 2008/0312581 A1 | 12/2008 | Hardy |
| 2008/0319375 A1 | 12/2008 | Hardy |
| 2009/0022806 A1 | 1/2009 | Mousa et al. |
| 2009/0074828 A1 | 3/2009 | Alexis et al. |
| 2009/0092582 A1 | 4/2009 | Bogin et al. |
| 2009/0124534 A1 | 5/2009 | Reineke |
| 2009/0142348 A1 | 6/2009 | De Sauvage et al. |
| 2009/0148384 A1 | 6/2009 | Fischer et al. |
| 2009/0155349 A1 | 6/2009 | Heller et al. |
| 2009/0169521 A1 | 7/2009 | Levenberg et al. |
| 2009/0196876 A1 | 8/2009 | De Sauvage et al. |
| 2009/0214618 A1 | 8/2009 | Schoenfisch et al. |
| 2009/0288176 A1 | 11/2009 | Bollinger et al. |
| 2009/0293137 A1 | 11/2009 | Combs et al. |
| 2009/0306225 A1 | 12/2009 | Lichter et al. |
| 2009/0313707 A1 | 12/2009 | Combs et al. |
| 2010/0015050 A1 | 1/2010 | Panyam et al. |
| 2010/0015228 A1 | 1/2010 | Lichter et al. |
| 2010/0015263 A1 | 1/2010 | Lichter et al. |
| 2010/0016218 A1 | 1/2010 | Lichter et al. |
| 2010/0021416 A1 | 1/2010 | Lichter et al. |
| 2010/0022661 A1 | 1/2010 | Lichter et al. |
| 2010/0028994 A1 | 2/2010 | Desimone et al. |
| 2010/0031378 A1 | 2/2010 | Edwards et al. |
| 2010/0035341 A1 | 2/2010 | Itskovitz-Eldor et al. |
| 2010/0048736 A1 | 2/2010 | Liu et al. |
| 2010/0068141 A1 | 3/2010 | Kaushal et al. |
| 2010/0068806 A1 | 3/2010 | Laine et al. |
| 2010/0076018 A1 | 3/2010 | Liu et al. |
| 2010/0111837 A1 | 5/2010 | Boyden et al. |
| 2010/0111846 A1 | 5/2010 | Boyden et al. |
| 2010/0111847 A1 | 5/2010 | Boyden et al. |
| 2010/0111848 A1 | 5/2010 | Boyden et al. |
| 2010/0111849 A1 | 5/2010 | Boyden et al. |
| 2010/0111850 A1 | 5/2010 | Boyden et al. |
| 2010/0111854 A1 | 5/2010 | Boyden et al. |
| 2010/0111855 A1 | 5/2010 | Boyden et al. |
| 2010/0111938 A1 | 5/2010 | Boyden et al. |
| 2010/0112011 A1 | 5/2010 | Friedberg |
| 2010/0112067 A1 | 5/2010 | Boyden et al. |
| 2010/0112068 A1 | 5/2010 | Boyden et al. |
| 2010/0113614 A1 | 5/2010 | Boyden et al. |
| 2010/0114348 A1 | 5/2010 | Boyden et al. |
| 2010/0114547 A1 | 5/2010 | Boyden et al. |
| 2010/0119557 A1 | 5/2010 | Boyden et al. |
| 2010/0121466 A1 | 5/2010 | Boyden et al. |
| 2010/0133615 A1 | 6/2010 | Mulfinger et al. |
| 2010/0143243 A1 | 6/2010 | Boyden et al. |
| 2010/0144641 A1 | 6/2010 | Popel et al. |
| 2010/0152651 A1 | 6/2010 | Boyden et al. |
| 2010/0152880 A1 | 6/2010 | Boyden et al. |
| 2010/0159020 A1 | 6/2010 | Breitenkamp et al. |
| 2010/0163576 A1 | 7/2010 | Boyden et al. |
| 2010/0168900 A1 | 7/2010 | Boyden et al. |
| 2010/0185174 A1 | 7/2010 | Boyden et al. |
| 2010/0187728 A1 | 7/2010 | Boyden et al. |
| 2010/0196280 A1 | 8/2010 | Fischer et al. |
| 2010/0196481 A1 | 8/2010 | Pritchard et al. |
| 2010/0203142 A1 | 8/2010 | Zhang et al. |
| 2010/0215760 A1 | 8/2010 | Kundu et al. |
| 2010/0233153 A1 | 9/2010 | Borromeo et al. |
| 2010/0256232 A1 | 10/2010 | White et al. |
| 2010/0260706 A1 | 10/2010 | Bogin et al. |
| 2010/0273864 A1 | 10/2010 | Lichter et al. |
| 2010/0331819 A1 | 12/2010 | Hossainy et al. |
| 2011/0008304 A1 | 1/2011 | Troyer et al. |
| 2011/0008417 A1 | 1/2011 | Ko |
| 2011/0008443 A1 | 1/2011 | Alsberg et al. |
| 2011/0020242 A1 | 1/2011 | Zheng et al. |
| 2011/0027172 A1 | 2/2011 | Wang et al. |
| 2011/0028172 A1 | 2/2011 | Wang et al. |
| 2011/0028181 A1 | 2/2011 | Byun et al. |
| 2011/0028395 A1 | 2/2011 | Popel et al. |
| 2011/0028945 A1 | 2/2011 | Amodei et al. |
| 2011/0034422 A1 | 2/2011 | Kannan et al. |
| 2011/0038939 A1 | 2/2011 | Lvov et al. |
| 2011/0052715 A1 | 3/2011 | Davis et al. |
| 2011/0061114 A1 | 3/2011 | Edwards et al. |
| 2011/0091534 A1 | 4/2011 | Breitenkamp et al. |
| 2011/0092668 A1 | 4/2011 | Breitenkamp et al. |
| 2011/0093960 A1 | 4/2011 | Edwards et al. |
| 2011/0097330 A1 | 4/2011 | Horner et al. |
| 2011/0130325 A1 | 6/2011 | Labhasetwar |
| 2011/0142941 A1 | 6/2011 | Davis et al. |
| 2011/0150765 A1 | 6/2011 | Boyden et al. |
| 2011/0152305 A1 | 6/2011 | Colson et al. |
| 2011/0172826 A1 | 7/2011 | Amodei et al. |
| 2011/0173708 A1 | 7/2011 | Combs et al. |
| 2011/0182883 A1 | 7/2011 | Combs et al. |
| 2011/0191865 A1 | 8/2011 | Edwards et al. |
| 2011/0200579 A1 | 8/2011 | Cunningham et al. |
| 2011/0200677 A1 | 8/2011 | Chandran et al. |
| 2011/0203013 A1 | 8/2011 | Peterson et al. |
| 2011/0236389 A1 | 9/2011 | Ni et al. |
| 2011/0244048 A1 | 10/2011 | Amiji et al. |
| 2011/0245207 A1 | 10/2011 | Skulachev |
| 2011/0252485 A1 | 10/2011 | De Sauvage et al. |
| 2011/0274620 A1 | 11/2011 | Harth et al. |
| 2011/0274747 A1 | 11/2011 | Habener et al. |
| 2011/0300532 A1 | 12/2011 | Johnen-Dechent et al. |
| 2012/0005766 A1 | 1/2012 | Bollinger et al. |
| 2012/0015039 A1 | 1/2012 | Sexton et al. |
| 2012/0021036 A1* | 1/2012 | Majeti ............ A61K 47/48238 424/422 |
| 2012/0021055 A1 | 1/2012 | Schoenfisch et al. |
| 2012/0027681 A1 | 2/2012 | Jung et al. |
| 2012/0030776 A1 | 2/2012 | Combs et al. |
| 2012/0034169 A1 | 2/2012 | Schoenfisch et al. |

(56) References Cited

U.S. PATENT DOCUMENTS

| | | |
|---|---|---|
| 2012/0045389 A1 | 2/2012 | Gassull Duro et al. |
| 2012/0046346 A1 | 2/2012 | Rossi et al. |
| 2012/0058505 A1 | 3/2012 | Helms et al. |
| 2012/0101738 A1 | 4/2012 | Boyden et al. |
| 2012/0107365 A1 | 5/2012 | Colson et al. |
| 2012/0109613 A1 | 5/2012 | Boyden et al. |
| 2012/0128783 A1 | 5/2012 | Boyden et al. |
| 2012/0156499 A1 | 6/2012 | Torchilin et al. |
| 2012/0174239 A1 | 7/2012 | Anderson et al. |
| 2012/0177701 A1 | 7/2012 | Ilyinskii et al. |
| 2012/0184495 A1 | 7/2012 | Koyakutty et al. |
| 2012/0210450 A1 | 8/2012 | De Sauvage et al. |
| 2012/0232012 A1 | 9/2012 | Popel et al. |
| 2012/0263722 A1 | 10/2012 | Ghayur et al. |
| 2012/0263793 A1 | 10/2012 | Vitaliano |
| 2012/0272341 A1 | 10/2012 | Combs et al. |
| 2012/0276133 A1 | 11/2012 | Maldonado |
| 2012/0276134 A1 | 11/2012 | Fraser et al. |
| 2012/0276155 A1 | 11/2012 | Kishimoto et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado |
| 2013/0245357 A1 | 9/2013 | Chauhan |
| 2013/0280205 A1 | 10/2013 | Mozaffari et al. |
| 2014/0303081 A1 | 10/2014 | Dhar et al. |
| 2016/0022825 A1 | 1/2016 | Dhar et al. |
| 2017/0000740 A9 | 1/2017 | Dhar et al. |

FOREIGN PATENT DOCUMENTS

| | | |
|---|---|---|
| WO | WO 03/087021 A2 | 10/2003 |
| WO | WO 03/103581 A2 | 12/2003 |
| WO | WO 2004/096140 A2 | 11/2004 |
| WO | WO 2005/019232 A1 | 3/2005 |
| WO | WO 2005/039534 A1 | 5/2005 |
| WO | WO 2005/058028 A2 | 6/2005 |
| WO | WO 2005/039534 A8 | 9/2005 |
| WO | WO 2005/079566 A2 | 9/2005 |
| WO | WO 2005/107818 A2 | 11/2005 |
| WO | WO 2005/112619 A2 | 12/2005 |
| WO | WO 2006/012201 A1 | 2/2006 |
| WO | WO 2006/026222 A2 | 3/2006 |
| WO | WO 2006/049854 A2 | 5/2006 |
| WO | WO 2006/079014 A2 | 7/2006 |
| WO | WO 2006/079120 A2 | 7/2006 |
| WO | WO 2006/098887 A2 | 9/2006 |
| WO | WO 2006/105403 A2 | 10/2006 |
| WO | WO 2006/107903 A2 | 10/2006 |
| WO | WO 2006/117675 A1 | 11/2006 |
| WO | WO 2006/127987 A2 | 11/2006 |
| WO | WO 2006/128121 A2 | 11/2006 |
| WO | WO 2006/132788 A2 | 12/2006 |
| WO | WO 2007/001962 A2 | 1/2007 |
| WO | WO 2007/014323 A2 | 2/2007 |
| WO | WO 2007/021423 A2 | 2/2007 |
| WO | WO 2007/033215 A2 | 3/2007 |
| WO | WO 2007/040469 A2 | 4/2007 |
| WO | WO 2007/080590 A2 | 7/2007 |
| WO | WO 2007/081608 A2 | 7/2007 |
| WO | WO 2007/101111 A2 | 9/2007 |
| WO | WO 2007/114979 A2 | 10/2007 |
| WO | WO 2007/120818 A2 | 10/2007 |
| WO | WO 2007/131128 A2 | 11/2007 |
| WO | WO 2007/133807 A2 | 11/2007 |
| WO | WO 2007/140483 A2 | 12/2007 |
| WO | WO 2008/013952 A2 | 1/2008 |
| WO | WO 2008/019357 A2 | 2/2008 |
| WO | WO 2008/036437 A2 | 3/2008 |
| WO | WO 2008/042469 A2 | 4/2008 |
| WO | WO 2008/048205 A2 | 4/2008 |
| WO | WO 2008/048288 A2 | 4/2008 |
| WO | WO 2008/051291 A2 | 5/2008 |
| WO | WO 2008/085828 A2 | 7/2008 |
| WO | WO 2008/087257 A1 | 7/2008 |
| WO | WO 2008/091465 A2 | 7/2008 |
| WO | WO 2008/091888 A2 | 7/2008 |
| WO | WO 2008/103409 A2 | 8/2008 |
| WO | WO 2008/106646 A2 | 9/2008 |
| WO | WO 2008/124632 A1 | 10/2008 |
| WO | WO 2008/127352 A2 | 10/2008 |
| WO | WO 2008/140507 A9 | 11/2008 |
| WO | WO 2008/143633 A2 | 11/2008 |
| WO | WO 2008/147481 A1 | 12/2008 |
| WO | WO 2009/009591 A9 | 1/2009 |
| WO | WO 2009/012303 A2 | 1/2009 |
| WO | WO 2009/023270 A2 | 2/2009 |
| WO | WO 2009/033130 A1 | 3/2009 |
| WO | WO 2009/046446 A2 | 4/2009 |
| WO | WO 2009/047587 A1 | 4/2009 |
| WO | WO 2009/073984 A1 | 6/2009 |
| WO | WO 2009/110939 A2 | 9/2009 |
| WO | WO 2009/132050 A2 | 10/2009 |
| WO | WO 2010/008995 A2 | 1/2010 |
| WO | WO 2010/011605 A2 | 1/2010 |
| WO | WO 2010/036961 A1 | 4/2010 |
| WO | WO 2010/042823 A1 | 4/2010 |
| WO | WO 2010/054264 A1 | 5/2010 |
| WO | WO 2010/054326 A2 | 5/2010 |
| WO | WO 2010/062413 A1 | 6/2010 |
| WO | WO 2010/074992 A2 | 7/2010 |
| WO | WO 2010/080557 A1 | 7/2010 |
| WO | WO 2010/083337 A2 | 7/2010 |
| WO | WO 2010/105058 A1 | 9/2010 |
| WO | WO 2010/111517 A1 | 9/2010 |
| WO | WO 2010/125115 A1 | 11/2010 |
| WO | WO 2010/143942 A1 | 12/2010 |
| WO | WO 2010/148007 A9 | 12/2010 |
| WO | WO 2011/082432 A1 | 7/2011 |
| WO | WO2011/084620 A2 | 7/2011 |
| WO | WO 2011/109600 A1 | 9/2011 |
| WO | WO 2011/115602 A1 | 9/2011 |
| WO | WO 2011/119901 A1 | 9/2011 |
| WO | WO 2011/130624 A2 | 10/2011 |
| WO | WO 2011/133925 A2 | 10/2011 |
| WO | WO 2011/153348 A2 | 12/2011 |
| WO | WO 2012/061466 A2 | 5/2012 |
| WO | WO 2012/075337 A2 | 6/2012 |
| WO | WO 2012/078745 A1 | 6/2012 |
| WO | WO 2012/092569 | 7/2012 |
| WO | WO 2012/106281 A2 | 8/2012 |
| WO | WO 2012/109466 A2 | 8/2012 |
| WO | WO 2012/135848 A2 | 10/2012 |
| WO | WO 2012/138570 A2 | 10/2012 |
| WO | WO 2012/142511 A2 | 10/2012 |
| WO | WO 2012/149252 A2 | 11/2012 |
| WO | WO 2012/149259 A1 | 11/2012 |
| WO | WO 2012/149265 A2 | 11/2012 |
| WO | WO 2012/149282 A2 | 11/2012 |
| WO | WO 2012/149301 A2 | 11/2012 |
| WO | WO 2012/149393 A9 | 11/2012 |
| WO | WO 2012/149405 A2 | 11/2012 |
| WO | WO 2012/149454 A2 | 11/2012 |
| WO | WO 2013/012628 A2 | 1/2013 |
| WO | WO 2013/033513 A1 | 3/2013 |
| WO | WO 2013/123298 A1 | 8/2013 |
| WO | WO 2014/059022 A1 | 4/2014 |
| WO | WO 2014/124425 A1 | 8/2014 |
| WO | WO 2014/169007 A2 | 10/2014 |
| WO | WO 2015/138992 A1 | 9/2015 |
| WO | WO 2016/022462 A1 | 2/2016 |

OTHER PUBLICATIONS

International Preliminary Report on Patentability for PCT/US2012/053307, dated Mar. 4, 2014. 2 pages total.
International Search Report/Written Opinion for PCT/US2012/053307, dated Jan. 18, 2013. 10 pages total.
Agemy et al. "Targeted nanoparticle enhanced proapoptotic peptide as potential therapy for glioblastoma" 2011. *Proc Natl Acad Sci USA.* 108(42):17450-17455.

(56) References Cited

OTHER PUBLICATIONS

Butera et al. "Peptidic targeting of phosphatidylserine for the MRI detection of apoptosis in atherosclerotic plaques". 2009. *Mol. Pharm.* 6:1903-1919.

Chalmers et al. "Selective uncoupling of individual mitochondria within a cell using a mitochondria-targeted photoactivated protonophore" 2012. *J. Am Chem Soc.* 134(2):758-761.

Dhar et al. "Targeted delivery of a cisplatin prodrug for safer and more effective prostate cancer therapy in vivo". 2011. *Proc.Natl. Acad.Sci.USA.* 108(5):1850-1855.

Fulda et al. "Targeting Mitochondria for cancer therapy". 2010. *Nature Reviews—Drug Discovery.* 9:447.

Gomes et al. "Characterization of PLGA microparticles as a drug carrier for 3-ethoxycarbonyl-2h-benzofuro[3,2-f]-1-benzopyran-2-one. Ultrastructural study of cellular uptake and intracellular distribution" 2006. *Drug Deliv.* 13(6):447-454.

Gosh et al. "Nanocapsulated curcumin: oral chemopreventive formulation against diethylnitrosamine induced hepatocellular carcinoma in rat". 2012. *Chem. Biol. Interact.* 195(3):206-214.

Hoye et al. "Targeting mitochondria". 2008. *Acc Chem Res.* 41(1):87-97.

International Patent Application No. PCT/US2013/026299, filed Feb. 15, 2013; International Search Report / Written Opinion dated Apr. 12, 2013; 9 pages.

International Patent Application No. PCT/US2013/026299, filed Feb. 15, 2013; International Preliminary Report on Patentability dated Aug. 28, 2014; 2 pages.

Kolishetti et al. "Engineering of self-assembled nanoparticle platform for precisely controlled combination drug therapy" 2010. *Proc.Natl.Acad.Sci.USA.* 107(42):17939-17944.

Marrache et al. "Engineering of blended nanoparticle platform for delivery of mitochondria-acting therapeutics" 2012. *Proc Natl. Acad Sci USA*, 109(40):16288-16293.

Marrache et al. "Engineered Nanoparticles for Mitochondria Trafficking of Drugs". 4 pages.

Melo et al. "Nanocytotoxicity: violacein and violacein-loaded poly (D, L-lactide-co-glycolide) nanoparticles acting on human leukemic cells". 2009. *J. Biomed Nanotechnol.* 5(2):192-201.

Murphy et al. "Targeting antioxidants to mitochondria by conjugation to lipophilic cations". 2007. *Annu Rev Pharmacol Toxicol.* 47:629-656.

Porteous et al. "Rapid uptake of lipophilic triphenylphosphonium cations by mitochondria in vivo following intravenous injection: implications for mitochondria-specific therapies and probes", 2010. *Biochim Biophys Acta.* 1800(9):1009-1017.

Prime et al. "A mitochondria-targeted S-nitrosothiol modulates respiration, nitrosates thiols, and protects against ischemia-reperfusion injury" 2009. *Proc Natl Acad Sci USA.* 106(26):10765-10769.

Ross et al. "Lipophilic triphenylphosphonium cations as tools in mitochondrial bioenergetics and free radical biology" 2005. *Biochemistry (Mosc).* 70(2):222-230.

Salvador-Morales et al. "Immuncompatibility Properties of Lipid-Polymer Hybrid Nanoparticles with Heterogeneous Surface Functional Groups". 2009. *Biomaterials.* 30:2231-2240.

Smith et al. "Delivery of bioactive molecules to mitochondria in vivo". 2003. *Proc Natl Acad Sci USA.* 100(9):5407-5412.

Smith et al. "Selective targeting of an antioxidant to mitochondria". 1999. *Eur J. Biochem.* 263(3):709-716.

Swamakar et al. "Oral bioavailability, therapeutic efficacy and reactive oxygen species scavenging properties of coenzyme Q10-loaded polymeric nanoparticles". 2011. *Biomaterials.* 32(28):6860-6874.

Wang et al. "Alpha-tocopheryl polyethylene glycol succinate-emulsified poly(lactic-co-glycolic acid) nanoparticles for reversal of multidrug resistance in vitro". *Nanotechnology.* 2012. 23(49):495103.

Higuchi et al., "Mannosylated semiconductor quantum dots for the labeling of macrophages" J Control Release, Jan. 22, 2008; 125(2):131-6. Available Online Oct. 17, 2007.

Park et al., "A new atherosclerotic lesion probe based on hydrophobically modified chitosan nanoparticles functionalized by the atherosclerotic plaque targeted peptides" J Control Release, Jun. 24, 2008; 128(3):217-23. Available Online Mar. 28, 2008.

Extended European Search Report for EP 12 82 9002, derived from PCT/US2012/053307, dated May 22, 2015; 8 pages.

Liu et al., "Interactions of serum proteins with small unilamellar liposomes composed of dioleoylphosphatidylethanolamine and oleic acid: high-density lipoprotein, apolipoprotein A1, and amphipathic peptides stabilize liposomes" Biochemistry, Apr. 17, 1990; 29(15):3637-43.

International Patent Application No. PCT/US2014/015744, filed Feb. 11, 2014; International Search Report and Written Opinion dated May 26, 2014; 15 pages.

International Patent Application No. PCT/US2014/015744, filed Feb. 11, 2014; International Preliminary Report on Patentability dated Aug. 20, 2015; 10 pages.

International Patent Application No. PCT/US2014/033431, filed Apr. 9, 2014; International Search Report and Written Opinion dated Oct. 27, 2014; 15 pages.

International Patent Application No. PCT/US2014/033431, filed Apr. 9, 2014; International Preliminary Report on Patentability dated Oct. 22, 2015; 11 pages.

European Patent Application No. 14 78 2682, filed Oct. 26, 2015; Supplementary European Search Report dated Sep. 2, 2016; 5 pages.

European Patent Application No. 13 74 9000.9, filed Sep. 5, 2014; Extended European Search Report and Search Opinion dated Sep. 21, 2015; 13 pages.

International Patent Application No. PCT/US2015/020591, filed Mar. 12, 2015; International Search Report and Written Opinion dated Jun. 10, 2015; 9 pages.

International Patent Application No. PCT/US2015/020591, filed Mar. 12, 2015; International Preliminary Report on Patentability dated Sep. 22, 2016; 6 pages.

International Patent Application No. PCT/US2015/043398, filed Aug. 3, 2015; International Search Report and Written Opinion dated Nov. 9, 2015; 8 pages.

International Patent Application No. PCT/US2015/043398, filed Aug. 3, 2015; International Preliminary Report on Patentability dated Feb. 16, 2017; 4 pages.

Abbott, "Astrocyte-endothelial interactions and blood-brain barrier permeability" J Anat, Jun. 2002; 200(6):629-38.

Aggarwal et al., "A dimeric Peptide that Binds Selectively to Prostate-Specific Membrane Antigen and Inhibits its Enzymatic Activity" Cancer Research, Sep. 2006; 23 pages.

Alexis et al. (2008) Factors affecting the clearance and biodistribution of polymeric nanoparticles. *Mol Pharm* 5(4):505-515.

Alexis F, et al. (2008) HER-2-Targeted Nanoparticle-Affibody Bioconjugates for Cancer Therapy. *ChemMedChem.*

Ammirante M, Luo JL, Grivennikov S, Nedospasov S, & Karin M (2010) B-cell-derived lymphotoxin promotes castration-resistant prostate cancer. Nature 464(7286):302-305.

Arvizo et al., "Gold Nanoparticles: Opportunities and Challenges in Nanomedicine" Expert Opin. Drug Deliv., 2010; 7:753-63.

Arvizo et al., "Inhibition of Tumor Growth and Metastasis by a Self-Therapeutic Nanoparticle" Proc. Natl. Acad. Sci. USA, 2013; 110:6700-5.

Attard G, Richards J, & de Bono JS (2011) New strategies in metastatic prostate cancer: Targeting the androgen receptor signaling pathway. Clin. Cancer Res. 17(7):1649-1657.

Baas et al., "Slipping Therapeutics to the Mitochondria" SciBX 5(38), Published online Sep. 27, 2012. 4 pages.

Bagalkot V, et al. (2007) Quantum dot-aptamer conjugates for synchronous cancer imaging, therapy, and sensing of drug delivery based on bi-fluorescence resonance energy transfer. *Nano Lett* 7(10):3065-3070.

Baker GL, Jiang X, Vogel EB, & Smith MR (2008) "Clickable" polyglycolides: Tunable synthons for thermoresponsive, degradable polymers. *Macromolecules* 41(6):1937-1944.

Beltran et al., "New therapies for castration-resistant prostate cancer: Efficacy and safety" Eur Urol, Aug. 2011; 60(2):279-90. Epub May 4, 2011.

(56) References Cited

OTHER PUBLICATIONS

Bertram Jp, et al. (2009) Functionalized poly(lactic-co-glycolic acid) enhances drug delivery and provides chemical moieties for surface engineering while preserving biocompatibility. *Acta Biornater*, 5(8):2860-2871.
Birsoy et al., "MCT1-Mediated Transport of a Toxic Molecule Is an Effective Strategy for Targeting Glycolytic Tumors" Nat. Genet., 2013; 45:104-8.
Biswas et al., "Liposomes loaded with paclitaxel and modified with novel triphenylphosphonium-PEG-PE conjugate possess low toxicity, target mitochondria and demonstrate enhanced antitumor effects in vitro and in vivo" J. Control. Rel., online Jan. 20, 2012, 159: 393-402.
Bolon et al., "STP position paper: Recommended practices for sampling and processing the nervous system (brain, spinal cord, nerve, and eye) during nonclinical general toxicity studies" Toxicol Pathol, 2013; 41(7):1028-48. Epub Mar. 7, 2013.
Bowman et al., "Trends in hospitalizations associated with pediatric traumatic brain injuries" *Pediatrics*, Nov. 2008; 122(5):988-93.
Braillon, "Re: Himisha Beltran, Tomasz M. Beer, Michael A. Carducci, et al. New therapies for castration-resistant prostate cancer: efficacy and safety. Eur urol 2011; 60:279-90" Eur Urol. Oct. 2011; 60(4):e33. Epub Jul. 13, 2011.
Brigger I, et al. (2004) Negative preclinical results with stealth nanospheres-encapsulated Doxorubicin in an orthotopic murine brain tumor model. *J Control Release*100(1):29-40.
Bustamante et al., "High Aerobic Glycolysis of Rat Hepatoma Cells in Culture: Role of Mitochondrial Hexokinase" Proc. Natl. Acad. Sci. USA, 1977; 74:3735-9.
Chan JM, et al. (2009) PLGA-lecithin-PEG core-shell nanoparticles for controlled drug delivery. *Biomaterials*30(8):1627-1634.
Chang SS, et al. (1999) Prostate-specific membrane antigen is produced in tumor-associated neovasculature. *Clin Cancer Res*5(10):2674-2681.
Chen, L. B., "Mitochondrial Membrane Potential in Living Cells" Annu. Rev. Cell. Biol., 1988; 4:155-81.
Chen et al, "Role of Mitochondria-Associated Hexokinase II in Cancer Cell Death Induced by 3-Bromopyruvate" Biochim. Biophys. Acta, 2009; 178:553-60.
Cheng J, et al. (2007) Formulation of functionalized PLGA-PEG nanoparticles for in vivo targeted drug delivery. *Biomaterials*28(5):869-876.
Chodobski et al., "Blood-brain barrier pathophysiology in traumatic brain injury" *Translational Stroke Research*, Dec. 2011; 2(4):492-516.
Chou et al., "Photodynamic Therapy: Applications in Atherosclerotic Vascular Disease with Motexafin Lutetium" Catheterization and Cardiovascular Interventions, 2002; 57:387-94.
Clementi et al., "Dendritic Poly(ethylene glycol) Bearing Paclitaxel and Alendronate for Targeting Bone Neoplasms" Molecular Pharmaceutics, May 24, 2011; 8:1063-72.
Coronado et al. "Surveillance for traumatic brain injury-related deaths--United States, 1997-2007." MMWR Surveill Summ, May 6, 2011; 60(5):1-32.
Dalla Libera et al. "IL-6 polymorphism associated with fatal outcome in patients with severe traumatic brain injury" Brain Inj, 2011; 25(4):365-69. Epub Feb. 11, 2011.
Daniel et al., "Intracellular distribution of psychotropic drugs in the grey and white matter of the brain: the role of lysosomal trapping" J Pharmacol, Oct. 2001; 134(4):807-14.
Dell'Antone, P., "Targets of 3-Bromopyruvate, a New, Energy Depleting, Anticancer Agent" Med. Chem., 2009; 5:491-6.
Dhar et al. (2008) Targeted delivery of cisplatin to prostate cancer cells by aptamer functionalized Pt(IV) prodrug-PLGA-PEG nanoparticles. *Proc Natl Acad Sci USA*105(45):17356-17361.
Dhar et al., "Polyvalent Oligonucleotide Gold Nanoparticle Conjugates as Delivery Vehicles for Platinum(IV) Warheads" J. Am. Chem. Soc., 2009; 131:14652-3.

dos Santos et al., "Control of lymphocyte adhesion to brain and aortic endothelium: ICAM-1, VCAM-1 and negative charge" J Neuroimmunol, May 1996; 66(1-2):125-34.
Du et al., "Dynamic regulation of mitochondrial function by glucocorticoids" Proc Natl Acad Sci USA, Mar. 3, 2009; 106(9):3543-8. Epub Feb. 6, 2009.
Duberstein et al., "Gait analysis in a pre- and post-ischemic stroke biomedical pig model" Physiol. Behay., Feb. 10, 2014; 125:8-16. Epub Nov. 25, 2013.
Duhaime et al., "Magnetic resonance imaging studies of age-dependent responses to scaled focal brain injury in the piglet" J Neurosurg, Sep. 2003; 99:542-8.
Dykman et al., "Gold nanoparticles inbiomedical applications: recent advances and perspectives" Chem Soc Rev, 2012; 41:2256-82.
de Gaetano Donati et al., "HIV infection, HAART, and endothelial adhesion molecules: current perspectives" Lancet Infect Dis, Apr. 2004; 4(4):213-222.
De Marzo et al., "Inflammation in prostate carcinogenesis" Nat Rev Cancer, Apr. 2007; 7(4):256-269.
Farokhzad OC, et al. (2004) Nanopartide-aptamer bioconjugates: A new approach for targeting prostate cancer cells. *Cancer Res*64(21):7668-7672.
Farokhzad OC, et al. (2006) Targeted nanoparticle-aptamer bioconjugates for cancer chemotherapy in vivo. *P Natl Acad Sci USA*103(16):6315-6320.
Ferlay et al., "Estimates of cancer incidence and mortality in Europe in 2008" Eur J Cancer, Mar. 2010; 46(4):765-781. Epub Jan. 29, 2010.
Fricke et al., "Mycobacteria Induce IFN-g Production in Human Dendritic Cells via Triggering of TLR2" J Immunol, 2006; 176-5173-82.
Frugier et al., "In situ detection of inflammatory mediators in post mortem human brain tissue after traumatic injury" J Neurotrauma, Mar. 2010; 27(3):497-507.
Fujimoto et al., "Novel therapeutic strategies following docetaxel-based chemotherapy in castration-resistant prostate cancer" Expert Rev Clin Pharmacol, Nov. 2010; 3(6):785-795.
Galsky et al. (2010) Cabazitaxel. *Nat Rev Drug Discov*9(9):677-678.
Galsky MD & Vogelzang NJ (2010) Docetaxel-based combination therapy for castration-resistant prostate cancer. *Ann Oncol*21(11):2135-2144.
Gerhardt WW, et al. (2006) Functional lactide monomers: methodology and polymerization. *Biomacromolecules*7(6):1735-1742.
Ghosh A & Heston WD (2004) Tumor target prostate specific membrane antigen (PSMA) and its regulation in prostate cancer. *J Cell Biochem*91(3):528-539.
Giljohann et al., "Gold Nanoparticles for Biology and Medicine" Angew. Chem. Int. Ed., 2010; 49:3280-94.
Gratton SE, et al. (2008) the effect of particle design on cellular internalization pathways. *Proc Nati Acad Sci USA*105(33):11613-11618.
Gref R, et al. (1994) Biodegradable long-circulating polymeric nanospheres. Science 263(5153):1600-1603.
Guadagno et al., "Microglia-derived TNFalpha induces apoptosis in neural precursor cells via transcriptional activation of the Bcl-2 family member Puma" Cell Death Dis, Mar. 14, 2013; 4:e538.
Gu F, et al. (2008) Precise engineering of targeted nanoparticles by using self-assembled biointegrated block copolymers. *Proc Natl Acad Sci U S A*105(7):25862591.
Herve et al., "CNS delivery via adsorptive transcytosis" AAPS J, Sep. 2008; 10(3):455-72. Epub Aug. 26, 2008.
Higgins et al., "Hypoxia and the Metabolic Phenotype of Prostate Cancer Cells" Biochim. Biophys. Acta, 2009; 1787:1433-43.
Hrkach et al., "Preclinical Development and Clinical Translation of a PSMA-Targeted Docetaxel Nanoparticle with a Differentiated Pharmacological Profile" Sci. Transl. Med., 2012; 4:128ra39.
Hsu, P. P.; Sabatini, D. M. Cancer Cell Metabolism: Warburg and Beyond. Cell 2008, 134, 703-7.

(56) References Cited

OTHER PUBLICATIONS

Hussain S, Pluckthun A, Allen TM, & Zangemeister-Wittke U (2007) Antitumor activity of an epithelial cell adhesion molecule targeted nanovesicular drug delivery system. *Mol Cancer Ther*6(11):3019-3027.
Jain RK (2001) Delivery of molecular and cellular medicine to solid tumors. *Adv Drug Deliv Rev*46(1-3):149-168.
Jain JP, Yenet Ayen W, Domb AJ, & Kumar N (2011) Biodegradable Polymers in Drug Delivery. *Biodegradable Polymers in Clinical Use and Clinical Development*, (John Wiley & Sons, Inc.), pp. 1-58.
Jemal et al., "Cancer statistics, 2010" CA Cancer J Clin, Sep.-Oct. 2010; 60(5):277-300. Epub Jul. 7, 2010.
Jia et al. (2009) Mechanisms of drug combinations: interaction and network perspectives. *Nat Rev Drug Discov*8(2): 111-128.
Jing F & Hillmyer MA (2008) A bifunctional monomer derived from lactide for toughening polylactide. *J Am Chem Soc*130(42):13826-13827.
Kalayci et al., "Effect of Coenzyme Q10 on ischemia and meuronal damage in an experiental traumatic brian-injurt omdel in rats" BMC Neuroscience, 2011; 12:75 pp. 1-7.
Karakunnel J & Dahut W (2008) Castrate-resistant prostate cancer: the right targets and combinations. *Therapy*5(1):57-61.
Khor et al. (2007) COX-2 expression predicts prostate-cancer outcome: analysis of data from the RTOG 92-02 trial. *Lancet Oncol*8(10):912-920.
Kingshott et al., "Surfaces That Resist Bioadhesion" Curr. Opin. Solid State Mater. Sci., 1999; 4:403-12.
Kinnunen et al., "White matter damage and cognitive impairment after traumatic brain injury" Brain, Feb. 2011; 134(Pt 2):449-63. Epub Dec. 29, 2010.
Kirpotin DB, et al. (2006) Antibody targeting of long-circulating lipidic nanoparticles does not increase tumor localization but does increase internalization in animal models. *Cancer Res*66(13):6732-6740.
Knoblach et al., "Interleukin-10 improves outcome and alters proinflammatory cytokine expression after experimental traumatic brain injury" Exp Neurol, Sep. 1998; 153(1):143-51.
Kong G, Braun RD, & Dewhirst MW (2000) Hyperthermia enables tumor-specific nanoparticle delivery: effect of particle size. *Cancer Res*60(16):4440-4445.
Kossmann et al., "Intrathecal and serum interleukin-6 and the acute-phase response in patients with severe traumatic brain injuries" Shock, Nov. 1995; 4(5):311-7.
Kuluz et al., "New pediatric model of ischemic stroke in infant piglets by photothrombosis: acute changes in cerebral blood flow, microvasculature, and early histopathology" Stroke, Jun. 2007; 38(6):1932-7.
Kumar et al., "Neuroinflammation after traumatic brain injury: opportunities for therapeutic intervention" Brain Behav Immun, 2012 Nov; 26(8):1191-201. Epub Jun. 21, 2012.
Langer R (2001) Drug delivery. Drugs on target. *Science*293(5527):58-59.
Laurent BA & Grayson SM (2011) Synthesis of Cyclic Dendronized Polymers via Divergent "Graftfrom" and Convergent Click "Graft-to" Routes: Preparation of Modular Toroidal Macromolecules. *J Am Chem Soc*.
Lee et al., "Anti-inflammatory and neuroprotective effects of triptolide on traumatic brain injury in rats" Respir Physiol Neurobiol, Jun. 15, 2012; 182(1):1-8. Epub Feb. 17, 2012.
Li X, Guo J, Asong J, Wolfert MA, & Boons GJ (2011) Multifunctional surface modification of goldstabilized nanoparticles by bioorthogonal reactions. *J Am Chem Soc*133(29): 11147-11153.
Lind et al., "The use of pigs in neuroscience: modeling brain disorders" Neurosci Biobehav Rev, 2007; 31(5):728-51. Epub Mar. 4, 2007.
Loane et al., "Neuroprotection for traumatic brain injury: translational challenges and emerging therapeutic strategies" Trends Pharmacol Sci., Dec. 2010; 31(12):596-604. Epub Oct. 29, 2010.

Ma et al., "Transplantation of neural stem cells enhances expression of synaptic protein and promotes functional recovery in a rat model of traumatic brain injury" Mol Med Rep, Sep.-Oct. 2011; 4(5):849-56. Epub Jun. 16, 2011.
Maas et al. "Clinical trials in traumatic brain injury: past experience and current developments" Neurotherapeutics, Jan. 2010; 7(1):115-26.
Madu et al., "Review: Novel diagnostic biomarkers for prostate cancer" J Cancer, 2010; 1:150-177.
Mamo et al., "Emerging nanotechnology approaches for HIV/AIDS treatment and prevention" Nanomedicine, 2010; 5(2):269-285.
Marrache et al., "Functionalized Polymers for Mitochondria Trafficking of Nanoparticles" Methods Mol Biol, 2012; 1265:103-12.
Marrache et al., "Immune stimulating photoactive hybrid nanoparticles for metastatic breast cancer" Integr Biol, 2013; 5:215-23.
Marrache et al., "Ex Vivo Programming of Dendritic Cells by Mitochondria-Targeted Nanoparticles to Produce Interferon-Gamma for Cancer Immunotherapy" ACS Nano, 2013; 7:7392-402.
Marrache et al., "Detouring of cisplatin to access mitochondrial genome for overcoming resistance" Proc Natl Acad Sci USA, Jul. 22, 2014; 111(29):10444-9. Epub Jul. 7, 2014.
Marrache et al., "Ex vivo generation of functional immune cells by mitochondria-targeted photosensitization of cancer cells" Methods Mol Biol, 2015; 1265:113-22.
Marrache et al., "The energy blocker inside the power house: Mitochondria targeted delivery of 3-bromopyruvae" Chem Sci, Mar. 2015; 6(3):1832-45.
Marrache et al., "The Energy Blocker inside the Power House: Mitochondria targeted delivery of 3-bromopyruvate" Supporting Information. Chem Sci, 2014; 14 pages.
Mathupala et al., "Hexokinase II: Cancer's Double-Edged Sword Acting as Both Facilitator and Gatekeeper of Malignancy When Bound to Mitochondria" Oncogene, 2006; 25:4777-86.
Matsumura Y & Maeda H (1986) A new concept for macromolecular therapeutics in cancer chemotherapy: mechanism of tumoritropic accumulation of proteins and the antitumor agent smancs. *Cancer Res*46(12 Pt 1):6387-6392.
Mayo Clinic Staff. "Traumatic Brain Injury" accessed Jun. 7, 2017 <mayoclinc.org/diseases-conditions/traumatic-brain-injury/basics/prevention/con-20029302?p=1> 13 pages.
McConeghy et al., "A review of neuroprotection pharmacology and therapies in patients with acute traumatic brain injury" CNS Drugs, Jul. 1, 2012; 26(7):613-36.
McManus et al., "The Mitochondria-Targeted Antioxidant MitoQ Prevents Loss of Spatial memory Retention and Early Neuropathology in a Transgenic Mouse Model of Alzheimer's Disease" J Neuroscience, Nov. 2, 2011; 31(44):15703-15.
Milowsky MI, et al. (2007) Vascular targeted therapy with anti-prostate-specific membrane antigen monoclonal antibody J591 in advanced solid tumors. *J Clin Oncol*25(5):540-547.
Missios et al., "Scaled cortical impact in immature swine: effect of age and gender on lesion volume" J Neurotrauma, Nov. 2009; 26(11):1943-51.
Modica-Napolitano et al., "Delocalized Lipophilic Cations Selectively Target the Mitochondria of Carcinoma Cells" Adv. Drug Deliv. Rev., 2001; 49:63-70.
Morgan et al., "Mitochondria-based photodynamic anti-cancer therapy" Adv Drug Deliv Reviews, 2001; 49:71-86.
Morris MJ, et al. (2007) Phase I evaluation of J591 as a vascular targeting agent in progressive solid tumors. *Clin Cancer Res*13(9):2707-2713.
Nakashima et al., "Purification and Characterization of a Bindable Form of Mitochondrial Bound Hexokinase from the Highly Glycolytic AS-30D Rat Hepatoma Cell Line" Cancer Res., 1988; 48:913-9.
Narayan et al., "Clinical trials in head injury" J Neurotrauma, May 2002; 19(5):503-57.
Norrish et al., "Non-Steroidal anti-inflammatory drugs and prostate cancer progression" Int J Cancer, 1998; 77:511-5.
Oda et al., "Preparation of a water-soluble fluorinated zinc phthalocyanine and its effect for photodynamic therapy" J Photochem Photobiol B: Biology, 2000; 59:20-25.

(56) References Cited

OTHER PUBLICATIONS

Oldendorf et al., "The large apparent work capability of the blood-brain barrier: a study of the mitochondrial content of capillary endothelial cells in brain and other tissues of the rat" Ann Neurol, May 1977; 1(5)409-17.
Owens DE & Peppas NA (2006) Opsonization, biodistribution, and pharmacokinetics of polymeric nanoparticles. *Int J Pharmaceut*307(1):93-102.
Pan et al., "Gold Nanoparticles of Diameter 1.4 Nm Trigger Necrosis by Oxidative Stress and Mitochondrial Damage" Small, 2009; 5:2067-76.
Pastorino et al., "Mitochondrial Binding of Hexokinase II Inhibits Bax-Induced Cytochrome C Release and Apoptosis" J. Biol. Chem., 2002; 277:7610-8.
Pathak et al., "The Prodrug platin-A: simultaneous release of cisplatin and aspirin" Agnew Chem Int Ed Engl, Feb. 10, 2014; 53(7):1963-7.
Pedersen et al., "Mitochondrial Bound Type II Hexokinase: A Key Player in the Growth and Survival of Many Cancers and an Ideal Prospect for Therapeutic Intervention" Biochim. Biophys. Acta, 2002; 1555:14-20.
Pedersen, "3-Bromopyruvate (3BP) a Fast Acting, Promising, Powerful, Specific, and Effective "Small Molecule" Anti-Cancer Agent Taken from Lab side to Bedside: Introduction to a Special Issue" J. Bioenerg. Biomembr., 2012; 44:1-6.
Perez-Pinzon et al., "CGS 19755 (Selfotel): A Novel Neuroprotective Agent Against CNS Injury" CNS Drug Rev, Sep. 1, 1996; 2(3):257-68.
Petrylak DP, et at. (2004) Docetaxel and estramustine compared with mitoxantrone and prednisone for advanced refractory prostate cancer. *N Engl J Med*351(15):1513-1520.
Pirollo KF & Chang EH (2008) Does a targeting ligand influence nanoparticle tumor localization or uptake? *Trends Biotech*26(10):552-558.
Platt et al., "Development and characterization of a Yucatan miniature biomedical pig permanent middle cerebral artery occlusion stroke model" Exp Transl Stroke Med, Mar. 23, 2014; 6(1):5.
Porporato et al., "Anticancer Targets in the Glycolytic Metabolism of Tumors: A Comprehensive Review" Front. Pharmacol., 2011; 2:49.
Porteous et al., "P-glycoprotein (Mdrla/lb) and breast cancer resistance protein (Bcrp) decrease the uptake of hydrophobic alkyl triphenylphosphonium cations by the brain" Biochim Biophys Acta, Jun. 2013; 1830(6):3458-65. Epub Feb. 21, 2013.
Pujol et al., (2010) Unveiling the role of network and systems biology in drug discovery. *Trends Pharmacol Sci*31(3) : 115-123.
Pun SH, et al. (2004) Targeted delivery of RNA-cleaving DNA enzyme (DNAzyme) to tumor tissue by transferrin-modified, cyclodextrin-based particles. *Cancer Biol Ther*3(7):641-650.
Quinzii et al., "Coenzyme Q and mitochondrial disease" Developmental disabilities research reviews, Jun. 2010; 16(2):183-8.
Ransohoff et al., "Innate immunity in the central nervous system" J Clin Invest, Apr. 2, 2012; 122(4):1164-71.
Raslan et al., "Medical management of cerebral edema" Neurosurg Focus, May 15, 2007; 22(5):E12.
Rosi et al., "Oligonucleotide-Modified Gold Nanoparticles for Intracellular Gene Regulation" Science, 2006; 312:1027-30.
Seferos et al. "Polyvalent DNA Nanoparticle Conjugates Stabilize Nucleic Acids" Nano Lett., 2009; 9:308-11.
Shamash J, et al. (2010) A validated prognostic index predicting response to dexamethasone and diethylstilbestrol in castrate-resistant prostate cancer. *Cancer*116(15):3595-3602.
Sharma et al., "Design and Evaluation of multifunctional nanocarriers for selective delivery of coenzyme Q10 to Mitochondria" Biomacromolecules, Jan. 9, 2012; 13(1):239-52. Published online Dec. 16, 2011.
Shear et al., "Neural progenitor cell transplants promote long-term functional recovery after traumatic brain injury" Brain Res, Nov. 5, 2004; 1026(1):11-22.

Smith et al., "Pamidronate to Prevent Bone Loss During Androgen-Deprivation Therapy for Prostate Cancer" New Enlg J Med, Sep. 27, 2001; 345(13):948- 55.
Soppimath et al. (2001) Biodegradable polymeric nanoparticles as drug delivery devices. *J Controlled Rel*70(1-2): 1-20.
Sullivan et al., "Behavioral deficits and axonal injury persistence after rotational head injury are direction dependent" J Neurotrauma, Apr. 1, 2013; 30(7):538-45.
Summers et al., *Veterinary Neuropathology*, Mosby: St. Louis, MO; 1994. Cover page, title page and table of contents.
Tanaka et al., "Experimental model of lacunar infarction in the gyrencephalic brain the miniature pig: neurological assessment and histological, . immunohistochemical, and physiological evaluation of dynamic corticospinal tract deformation" Stroke, Jan. 2008; 39(1):205-12. Epub Nov. 29, 2007.
Taneja SS (2004) ProstaScint(R) Scan: Contemporary Use in Clinical Practice. *Rev Urol*6 Suppl 10:S19-28.
Tannock et al. (2004) Docetaxel plus prednisone or mitoxantrone plus prednisone for advanced prostate cancer. *N Engl J Med*351(15):1502-1512.
Uemura H, et al. (2010) Immunological evaluation of personalized peptide vaccination monotherapy in patients with castration-resistant prostate cancer. *Cancer Sci*101(3):601-608.
Ullen et al., "Additive/synergistic antitumoral effects on prostate cancer cells in vitro following treatment with a combination of docetaxel and zoledronic acid" Acta Oncologica, 2005; 44:644-50.
Vander Heiden et al., "Understanding the Warburg Effect: The Metabolic Requirements of Cell Proliferation" Science, 2009; 324:1029-33.
Verma A, et al. (2008) Surface-structure-regulated cell-membrane penetration by monolayer-protected nanoparticles. *Nature Mat*7(7):588-595.
Wallenquist et al., "Grafted neural progenitors migrate and form neurons after experimental traumatic brain injury" Restor Neurol Neurosci, 2009; 27(4):323-34.
Wang et al., "Photothermal Effects of Supramolecularly Assembled Gold Nanoparticles for the Targeted Treatment of Cancer Cells" Angew. Chem. Int. Ed., 2010; 49:3777-81.
Warburg, "On the Origin of Cancer Cells" Science, 1956; 123:309-14.
Watanabe et al., "MR-based statistical atlas of the Göttingen minipig brain" Neurolmage, Nov. 2001; 14(5):1089-96.
Weiss et al., "Coupling of biotin-(poly(ethylene glycol))amine to poly(D,L-lactide-co-glycolide) nanoparticles for versatile surface modification" Bioconjug Chem, Jul.-Aug. 2007;18(4):1087-94. Published Online Jun. 23, 2007.
Werner and Engelhard, "Pathophysiology of traumatic brain injury" Br J Anaesth, Jul. 2007; 99(1):4-9.
Wilson, "Isozymes of Mammalian Hexokinase: Structure, Subcellular Localization and Metabolic Function" J. Exp. Biol., 2003; 206:2049-57.
Wolburg et al., "Brain endothelial cells and the glio-vascular complex" Cell Tissue Res, Jan. 2009; 335(1):75-96.
Woodcock et al., "The role of markers of inflammation in traumatic brain injury" Front Neurol, Mar. 4, 2013; 4:18.
Wu P, et al. (2010) Adenovirus targeting to prostate-specific membrane antigen through virus-displayed, semirandom peptide library screening. *Cancer Res*70(23):9549-9553.
Xiong et al., "Increased brain injury and worsened neurological outcome in interleukin-4 knockout mice after transient focal cerebral ischemia" Stroke, Jul. 2011; 42(7):2026-32. Epub May 19, 2011.
Yakovlev and Faden, "Caspase-dependent apoptotic pathways in CNS injury" Mol Neurobiol, Aug.-Dec. 2001; 24(1-3):131-44.
Yan et al., "Post-traumatic hypoxia exacerbates neurological deficit, neuroinflammation and cerebral metabolism in rats with diffuse traumatic brain injury" J Neuroinflammation, Oct. 28, 2011; 8:147.
Yuan F, et al. (1994) Microvascular permeability and interstitial penetration of sterically stabilized (stealth) liposomes in a human tumor xenograft. *Cancer Res*54(13):3352-3356.
Yuan F, et al. (1995) Vascular permeability in a human tumor xenograft: molecular size dependence and cutoff size. *Cancer Res*55(17):3752-3756.

(56) References Cited

OTHER PUBLICATIONS

Zhang et al., "A universal scaling law between gray matter and white matter of cerebral cortex" Proc Natl Acad Sci USA, May 9, 2000; 97(10):5621-6.

Zhang L, et al. (2007) Co-delivery of hydrophobic and hydrophilic drugs from nanoparticle-aptamer bioconjugates. *ChemMedChem* 2(9):1268-1271.

Zhang L, et al. (2008) Self-assembled lipid--polymer hybrid nanoparticles: a robust drug delivery platform. *ACS nano* 2(8):1696-1702.

Zhao et al., "Highly Selective Mitochondria-Targeting Amphiphilic Silicone(IV) Phthalocyanines with Axially Ligated Rhodamine B for Photodynamic Therapy" Inorganic Chem, Dec. 22, 2011; 51:812-21.

Ziebell et al., "Involvement of pro- and anti-inflammatory cytokines and chemokines in the pathophysiology of traumatic brain injury" Neurotherapeutics, Jan. 2010; 7(1):22-30.

* cited by examiner

SEQUENCE LISTING

```
<160> NUMBER OF SEQ ID NOS: 6

<210> SEQ ID NO 1
<211> LENGTH: 6
<212> TYPE: PRT
<213> ORGANISM: artificial
<220> FEATURE:
<223> OTHER INFORMATION: polypeptide that binds (phosphatidylserine) PS

<400> SEQUENCE: 1

Leu Ile Lys Lys Pro Phe
1               5

<210> SEQ ID NO 2
<211> LENGTH: 6
<212> TYPE: PRT
<213> ORGANISM: artificial
<220> FEATURE:
<223> OTHER INFORMATION: polypeptide that binds (phosphatidylserine) PS

<400> SEQUENCE: 2

Pro Gly Asp Leu Ser Arg
1               5

<210> SEQ ID NO 3
<211> LENGTH: 6
<212> TYPE: PRT
<213> ORGANISM: artificial
<220> FEATURE:
<223> OTHER INFORMATION: polypeptide that binds (phosphatidylserine) PS

<400> SEQUENCE: 3

Asp Ala His Ser Phe Ser
1               5

<210> SEQ ID NO 4
<211> LENGTH: 7
<212> TYPE: PRT
<213> ORGANISM: artificial
<220> FEATURE:
<223> OTHER INFORMATION: polypeptide that binds (phosphatidylserine) PS

<400> SEQUENCE: 4

Gly Pro Leu Gly Val Arg Gly
1               5

<210> SEQ ID NO 5
<211> LENGTH: 18
<212> TYPE: PRT
<213> ORGANISM: artificial
<220> FEATURE:
<223> OTHER INFORMATION: polypeptide that binds (phosphatidylserine) PS

<400> SEQUENCE: 5

Phe Ala Glu Lys Phe Lys Glu Ala Val Lys Asp Tyr Phe Ala Lys Phe
1               5                   10                  15
```

```
Trp Asp

<210> SEQ ID NO 6
<211> LENGTH: 7
<212> TYPE: PRT
<213> ORGANISM: artificial
<220> FEATURE:
<223> OTHER INFORMATION: polypeptide that binds (phosphatidylserine) PS

<400> SEQUENCE: 6

Leu Ile Lys Lys Pro Phe Gly
1               5
```

APOPTOSIS-TARGETING NANOPARTICLES

RELATED APPLICATIONS

This application is the § 371 U.S. National Stage of International Application No. PCT/US2012/053307, filed Aug. 31, 2012, which claims the benefit of priority to U.S. Provisional Patent Application No. 61/529,637, filed on Aug. 31, 2011, each application is hereby incorporated herein in its entirety to the extent that it does not conflict with the present disclosure.

STATEMENT OF GOVERNMENTAL SUPPORT

This invention was made with government support under grant number 1P30GM092378, awarded by the NIH of the United States government. The government has certain rights in the invention.

FIELD

The present disclosure relates to nanoparticles configured to target apoptotic cells, particularly apoptotic macrophages of vascular plaques, and methods of use thereof, including diagnostic and therapeutic uses.

BACKGROUND

Atherothrombotic vascular disease (ATVD) remains the number one cause of death in the industrialized world, and this problem is growing annually due to the increasing rate of obesity and insulin resistance worldwide. Although oral drugs that lower systemic risk factors have been successful, there is a tremendous treatment gap that leaves up to 70% of the high-risk population at continued risk. A number of promising arterial-wall targets have been identified and validated using molecular-genetic approaches in animal models of atherosclerosis, but many of these are not amenable to oral or even standard systemic therapy.

Currently, there is no widely accepted diagnostic method to prospectively identify vulnerable plaques which could lead to ATVD. However, such prospective identification of vulnerable plaques could reduce the morbidity and mortality of thromboembolism.

Apoptosis, or programmed cell death is a genetically controlled process that contributes to the instability of atherosclerotic lesions. Apoptosis of the macrophages and of smooth muscle cells (SMC) play an important role in the process of plaque rupture and thrombus formation. Exposure of anionic phosphatidylserine (PS) on the outer leaflet of the cell membrane is one of the earliest molecular events in apoptosis. From the technical viewpoint, apoptosis will be an attractive target for the diagnosis of atherosclerotic plaques prone to thrombotic event as well as cancer.

The most common method of detecting PS on cell surface involves the use the Ca2+-dependent, PS-binding protein annexin V. For in vitro assays, the 35-kDa annexin V protein is typically labeled with a fluorescent dye, whereas radioactive and diffusion-weighted magnetic resonance imaging (MRI) techniques are employed for in vivo imaging. Although it is utilized extensively, the labeled annexin V protein is expensive and moderately unstable, and the application of diffusion-weighted MRI is limited because the method relies on strong magnetic field gradients and is sensitive to artifacts. Additionally, the magnitude of changes associated with annexin V diffusion-weighted MRI is small, making it difficult to discern the distinction between the tissue shrinkage, necrosis, and other processes that occur with an arterial wall vessel.

Other possible options for targeting PS include peptides that bind PS with high affinity and specificity and zinc 2,2'-dipicolylamine ($Zn^{2+}$-DPA) coordination complexes, which have been shown to mimic the apoptosis sensing function of annexin V.

An alternative approach to detection of PS translocation (as a proxy for apoptosis) is detection of the collapse of mitochondrial membrane potential ($\Delta\psi_m$). $\Delta\psi m$ is a hallmark of the initiating phase of apoptosis. Unlike the transient nature of PS exposure, collapse of $\Delta\psi_m$ is an ongoing process. $\Delta\psi_m$ monitoring could offer an effective strategy for detection of vulnerable plaques by monitoring apoptotic macrophages atherosclerotic plaques of arterial-wall leading to early diagnosis and aggressive management to help prevent or slow the progression by delivering therapeutics that exhibit direct effects on macrophage inflammation related to ATVD or coronary heart disease (CHD) in general.

SUMMARY

The present disclosure describes, among other things, nanoparticles that target apoptotic cells. In embodiments, the nanoparticles selectively target apoptotic macrophages. In embodiments, the nanoparticles are used for imaging and diagnosis of vulnerable plaques. In embodiments, the nanoparticles are used to deliver therapeutic agents to vulnerable plaques for targeted therapy.

The nanoparticles described herein contain one or more moieties configured to target or monitor apoptotic cells. Such moieties may be PS-targeting moieties or $\Delta\psi m$ monitoring moieties. The nanoparticles may also include one or more moieties configured to target macrophages. The nanoparticles may include one or more contrast agent for purpose of visualization, imaging, diagnosis, or the like. In addition, or alternatively, the nanoparticles may include one or more therapeutic agents configured to treat CHD, ATVD, or the like.

By targeting nanoparticles to apoptotic cells or apoptotic macrophages, the nanoparticles may accumulate in vascular plaques. If the nanoparticles include a contrast agent, visualization of accumulated nanoparticles may be used for the diagnosis of vulnerable plaques of ATVD. If the nanoparticles include a therapeutic agent, targeted therapy may be delivered for treatment of ATVD or CHD.

Advantages of one or more of the various embodiments presented herein over prior nanoparticles, imaging methodologies, treatment modalities, or the like will be readily apparent to those of skill in the art based on the following detailed description when read in conjunction with the accompanying drawings.

Figure 1A:
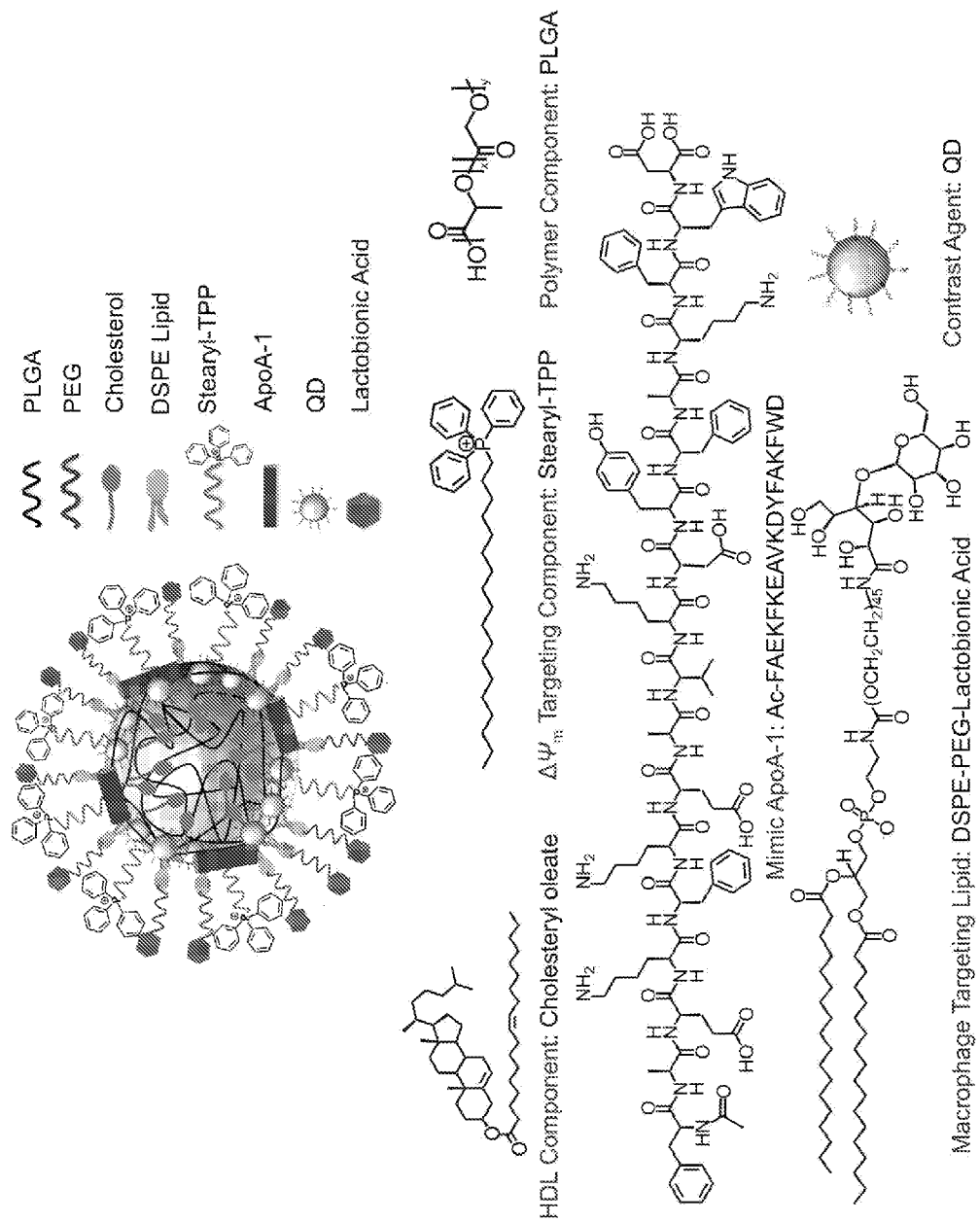
FIG. 1A is an overview of an embodiment of a reaction scheme for HDL-mimicking nanoparticles by nano-precipitation for atherosclerotic plaques.

The drawings in are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like.

As used herein, "treat" or the like means to cure, prevent, or ameliorate one or more symptom of a disease or condition.

As used herein, "lipid" includes phospholipid.

"Peptide" and "polypeptide" are used interchangeable herein.

As used herein, a compound that is "hydrophobic" is a compound that is insoluble in water or has solubility in water below 1 microgram/liter.

As used herein a compound that is "hydrophilic" is a compound that is water soluble or has solubility in water above 10 mg/liter.

As used herein, "bind," "bound," or the like means that chemical entities are joined by any suitable type of bond, such as a covalent bond, an ionic bond, a hydrogen bond, van der walls forces, or the like. "Bind," "bound," and the like are used interchangeably herein with "attach," "attached," and the like.

As used herein, a molecule to moiety "attached" to a core of a nanoparticle may be embedded in the core, contained within the core, attached to a molecule that forms at least a portion of the core, attached to a molecule attached to the core, or directly attached to the core.

As used herein, a "derivative" of a compound is a compound structurally similar to the compound of which it is a derivative. Many derivatives are functional derivatives. That is, the derivatives generally a desired function similar to the compound to which it is a derivative. By way of example, mannose is described herein as a macrophage targeting moiety because mannose binds macrophage mannose receptors. Accordingly, a functional mannose derivative is a mannose derivative that may bind a macrophage mannose receptor with the same or similar affinity as mannose (e.g., has dissociation constant that is within about a 100 fold range of that of mannose, such as within about a 10 fold range of that of mannose). By way of further example, triphenyl phosphonium (TPP) is described herein as a mitochondrial targeting moiety because it can accumulate, or cause a compound or complex (such as a nanoparticle) to which it is bound to accumulate, in the mitochondrial matrix. Accordingly, a functional derivative of TPP is a derivative of TPP that may accumulate, or cause a compound or complex to which it is bound to accumulate, in the mitochondrial matrix in a similar concentration as TPP (e.g., within about a 100 fold concentration range, such as within about a 10 fold concentration range).

Nanoparticles, as described herein, include a core and one or more targeting moieties, as well as one or more contrast agents or one or more therapeutic agents. In embodiments, the contrast agents or therapeutic agents are contained or embedded within the core. If the nanoparticle includes therapeutic agents, the agents are preferably released from the core at a desired rate. In embodiments, the core is biodegradable and releases the agents as the core is degraded or eroded. The targeting moieties preferably extend outwardly from the core so that they are available for interaction with cellular components, which interactions will target the nanoparticles to the appropriate cells, such as apoptotic cells; organelles, such as mitochondria; or the like. The targeting moieties may be tethered to the core or components that interact with the core.

I. Core

The core of the nanoparticle may be formed from any suitable component or components. Preferably, the core is formed from hydrophobic components such as hydrophobic polymers or hydrophobic portions or polymers or lipids. In embodiments, the core includes phospholipids which may form micelles having a hydrophobic core and a hydrophilic outer surface. The core may also or alternatively include block copolymers that have hydrophobic portions and hydrophilic portions that may self-assemble in an aqueous environment into particles having the hydrophobic core and a hydrophilic out surface. In embodiments, the core comprises one or more biodegradable polymer or a polymer having a biodegradable portion.

Any suitable synthetic or natural bioabsorbable polymers may be used. Such polymers are recognizable and identifiable by one or ordinary skill in the art. Non-limiting examples of synthetic, biodegradable polymers include: poly(amides) such as poly(amino acids) and poly(peptides); poly(esters) such as poly(lactic acid), poly(glycolic acid), poly(lactic-co-glycolic acid) (PLGA), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), fibrin, fibrinogen, cellulose, starch, collagen, and hyaluronic acid, copolymers and mixtures thereof. The properties and release profiles of these and other suitable polymers are known or readily identifiable.

In various embodiments, described herein the core comprises PLGA. PLGA is a well-known and well-studied hydrophobic biodegradable polymer used for the delivery and release of therapeutic agents at desired rates.

Preferably, the at least some of the polymers used to form the core are amphiphilic having hydrophobic portions and hydrophilic portions. The hydrophobic portions can form the core, while the hydrophilic regions may for a shell that helps the nanoparticle evade recognition by the immune system and enhances circulation half-life. Examples of amphiphilic polymers include block copolymers having a hydrophobic block and a hydrophilic block. In embodiments, the core is formed from hydrophobic portions of a block copolymer, a hydrophobic polymer, or combinations thereof.

Any suitable hydrophilic polymer may form a hydrophilic block of a block copolymer. Examples of suitable hydrophilic polymers include polysaccharides, dextran, chitosan, hyaluronic acid, and the like. In embodiments, polyethylene glycol (PEG) is a hydrophilic polymer used to serve as the hydrophilic portion of a block copolymer.

II. Targeting Moieties

The nanoparticles described herein include one or more moieties that target the nanoparticles to apoptotic cells or that allow for monitoring of apoptosis. In embodiments, the nanoparticles include a moiety that targets the nanoparticles to macrophages. The targeting moieties may be tethered to the core in any suitable manner, such as binding to a molecule that forms part of the core or to a molecule that is bound to the core.

In embodiments, a targeting moiety is bound to a hydrophilic polymer that is bound to a hydrophobic polymer that forms part of the core or that is bound to a lipid, such as a phospholipid, that is bound to, or forms part of, the core. In embodiments, a targeting moiety is bound to a hydrophilic portion of a block copolymer having a hydrophobic block that forms part of the core.

The hydrophilic polymers, or portions thereof, may contain, or be modified to contain, appropriate functional groups, such as —OH, —COOH, —NH$_2$, —SH, or the like, for reaction with and binding to the targeting moieties that have, or are modified to have, suitable functional groups.

Examples of targeting moieties tethered to polymers and lipids are presented throughout this disclosure for purpose of illustrating the types of reactions and tethering that may occur. However, one of skill in the art will understand that tethering of targeting moieties to polymers, lipids, polypeptides, or the like, may be carried out according to any of a number of known chemical reaction processes.

Targeting moieties may be present in the nanoparticles at any suitable concentration.

In embodiments, the concentration may readily be varied based on initial in vitro analysis to optimize prior to in vivo study or use. In embodiments, the targeting moieties will have surface coverage of from about 10% to about 100%.

a. Moieties for Targeting Apoptotic Cells

Any suitable moiety for targeting a nanoparticle to cells undergoing apoptosis or that are about to undergo apoptosis may be incorporated into the nanoparticle. In embodiments, the targeting moiety targets phosphatidylserine (PS). Because exposure of PS on the outer leaflet of the cell membrane is one of the earliest molecular events in apoptosis, targeting PS that has been translocated to the outer membrane may serve as a proxy for targeting apoptotic cells.

Any suitable moiety that targets PS may be used. In embodiments, the PS-targeting moiety is a polypeptide that binds PS with high affinity and specificity. Such polypeptides may be readily identified by one of skill in the art through any suitable mechanism, such as through the use of phage display libraries; e.g. as described in Butera et al. (2009), "Peptidic targeting of phosphatidylserine for the MRI detection of apoptosis in atherosclerotic plaques", Mol. Pharm. 6:1903-1919. Non-limiting examples of polypeptides that bind PS with a high affinity and specificity include polypeptides that include the following amino acid sequences LIKKPF (SEQ ID NO:1), PGDLSR (SEQ ID NO:2), DAHSFS (SEQ ID NO:3) or the like.

Preferably, the polypeptide includes an amino acid capable of conjugating to a pendant reactive group of the polymer. Examples of reactive groups that the polymer may have for reaction with a polypeptide include maleimide, glycidyl, isocyanate, isothiocyante, activated esters, activated carbonates, anhydride, sulfhydryl and the like. By way of example, any native or biomimetic amino acid having functionality that enables nucleophilic addition; e.g. via amide bond formation, may be included in polypeptide for purposes of conjugating to the polypeptide having a suitable reactive group. Lysine, homolysine, ornithine, diaminopropionic acid, and diaminobutanoic acid are examples of amino acids having suitable properties for conjugation to a reactive group of the polymer, such as carboxyl group. In addition, the N-terminal alpha amine of a polypeptide may be used to conjugate to a suitable reactive group of the polymer, if the N-terminal amine is not capped. By way of another example, disulfide bond formation between the polymer and the polypeptide may be used to bind the polypeptide to the polymer. Similar reaction strategies to those mentioned above for binding a polypeptide to a polymer may be used for binding a polypeptide to a lipid, such as a phospholipid.

In embodiments, a PS-targeting polypeptide is conjugated to a hydrophilic polymer, such as PEG. The hydrophilic polymer may be bound to a hydrophobic polymer, such as PLGA, that forms a part of the core of the nanoparticle or may be bound to a lipid, such as a phospholipid. The lipid may form part of the core or may be bound to the core through hydrophobic interactions. One example of a tethered PS-targeting moiety that may be used in accordance with the teachings herein is PLGA-b-PEG-LIKKPF having a structure as shown in Formula I:

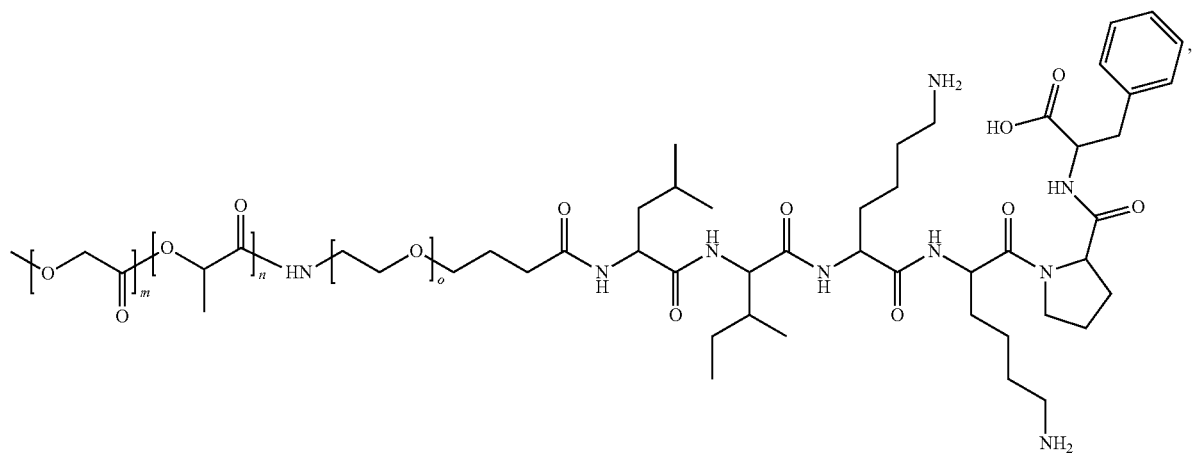

PLGA-b-PEG-LIKKPF where m, n, and o are any suitable integer. PLGA-COOH may be coupled to PEG-NH$_2$ to give PLGA-b-PEG. Coupling of the polypeptide to PEG may occur before or after coupling of PEG to PLGA. The PLGA may form a part of the core of the nanoparticle.

Another example of a tethered PS-targeting moiety that may be used in accordance with the teachings herein is distearoyl-snglycero-3-phosphoethanolamine (DSPE)-PEG-LIKKPF having a structure as shown in Formula II:

It will be understood that the compounds of Formulas I and II, which contain the PS-targeting moieties, are shown for purposes of illustration and that other polymers, phospholipids or PS-targeting polypeptides may be employed.

In embodiments, the PS-targeting moiety includes a zinc 2,2'-dipicolylamine (Zn$^{2+}$-DPA) coordination complex. Zn$^{2+}$-DPA complexes have been shown to mimic the apoptosis sensing function of annexin V. Zinc(II) readily forms a complex coordinated to the three nitrogen atoms of DPA.

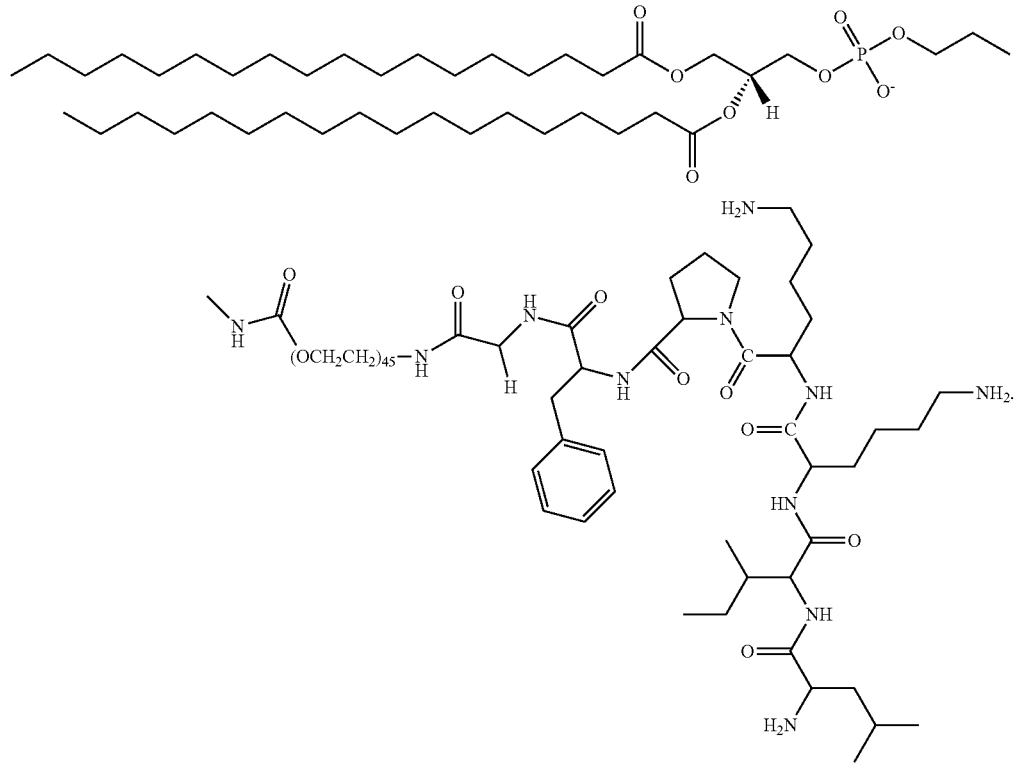

Zinc(II) is also a viable choice for a metal cation because it is not redox active, and it does not quench the fluorescence of an attached dye. The $Zn^{2+}$-DPA PS-targeting moiety may be conjugated to a hydrophilic polymer, such as PEG. The hydrophilic polymer may be bound to a hydrophobic polymer, such as PLGA, that forms a part of the core of the nanoparticle or may be bound to a lipid, such as a phospholipid. The lipid may form part of the core or may be bound to the core through hydrophobic interactions. One example of a tethered $Zn^{2+}$-DPA complex that may be used in accordance with the teachings herein is PLGA-b-PEG-Mal-DPA having a structure as shown in Formula III:

The degree of PS binding depends of the number of $Zn^{2+}$-DPA moieties in the nanoparticle. It has been shown that more $Zn^{2+}$-DPA binding motifs increase polar interactions among molecules and membranes, as well as produce a stronger response to PS. The $Zn^{2+}$-DPA preferably detects the bilayer membranes containing 5% PS or less, which is the fraction of PS that signals the onset of apoptosis. Other coordination complexes, those involving different arrangements of dipicolylamine and other dimetallic sensors, may be employed as an alternative to $Zn^{2+}$-DPA While not intending to be bound by theory, it is believed that the DPA moiety of PLGA-b-PEG-Mal-DPA may

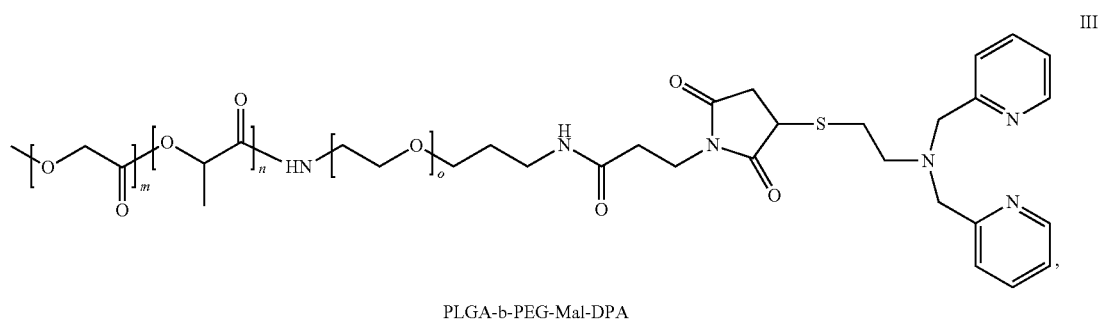

PLGA-b-PEG-Mal-DPA where m, n, and o are any suitable integer. The DPA moiety, such as 2-(bis(pyridine-2-ylmethyl)amino)ethanethiol, may be coupled to PEG using maleimide-PEG-$NH_2$ to give $NH_2$-PEG-Mal-DPA, which may be coupled to PLGA-COOH to give PLGA-b-PEG-Mal-DPA as shown in Formula III.

Another example of a tethered $Zn^{2+}$-DPA complex that may be used in accordance with the teachings herein is DSPE-PEG-Mal-DPA having a structure as shown in Formula IV:

become buried in the lipid layer and not be readily available for $Zn_{2+}$ binding. It has been found that conjugation of the DPA moiety to the phospholipid distearoyl-snglycero-3-phosphoethanolamine (DSPE) via a PEG intermediary to produce DSPE-PEG-Mal-DPA resulted in increased $Zn^{2+}$ binding relative to PLGA-b-PEG-Mal-DPA (data not shown).

B. Moieties for Monitoring Apoptosis—Mitochondrial Targeting

Any suitable moiety for monitoring apoptosis may be incorporated into a nanoparticle. In embodiments, the apop-

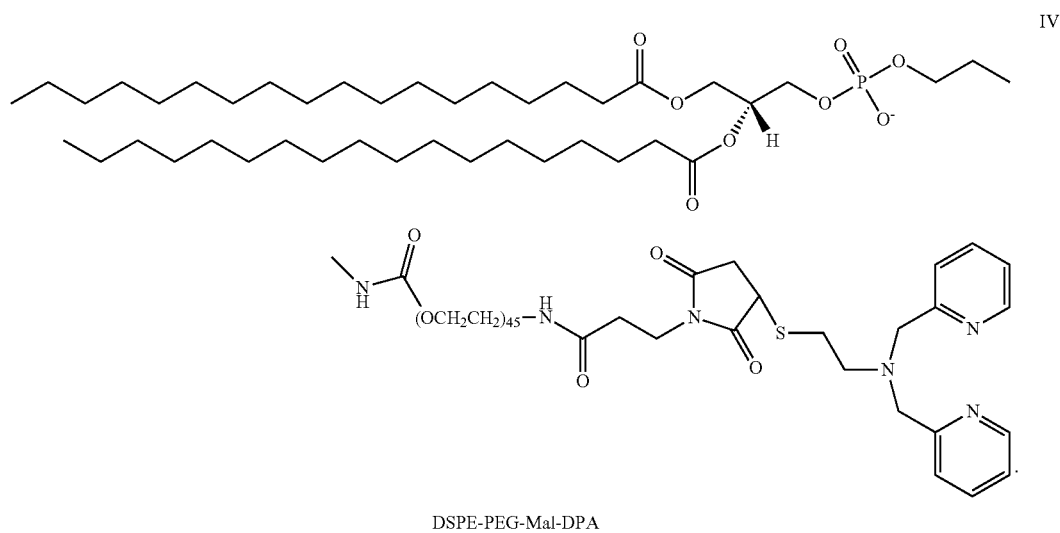

DSPE-PEG-Mal-DPA

It will be understood that the compounds of Formulas III and IV, which contain the DPA complex, are shown for purposes of illustration and that other polymers or phospholipids may be employed.

tosis monitoring moiety is a moiety that facilitates accumulation of the nanoparticle in the mitochondrial matrix. The collapse of mitochondrial membrane potential ($\Delta\psi m$) is a hallmark of the initiating phase of apoptosis. Upon collapse of the mitochondrial membrane, components of the mitochondrial matrix are released into the cytoplasm. Thus, if a nanoparticle having a suitable contrast agent is targeted to the mitochondrial matrix, Δωm (and thus initiation of apoptosis) may be detected by observing the spreading of the nanoparticle (via the contrast agent) from the mitochondrial matrix throughout the cytoplasm. By way of example, accumulation of the nanoparticles within the mitochondrial matrix would be indicative of non-apoptotic cells, while diffusely spreading of the nanoparticles throughout the cytoplasm would be indicative of cells in the initial stages of apoptosis.

Any suitable moiety for facilitating accumulation of the nanoparticle within the mitochondrial matrix may be employed. Due to the substantial negative electrochemical potential maintained across the inner mitochondrial membrane, delocalized lipophilic cations are effective at crossing the hydrophobic membranes and accumulating in the mitochondrial matrix. Triphenyl phosophonium (TPP) containing compounds can accumulate greater than 1000 fold within the mitochondrial matrix. Any suitable TPP-containing compound may be used as a mitochondrial matrix targeting moiety. Representative examples of TPP-based moieties may have structures indicated below in Formula V, Formula VI or Formula VII:

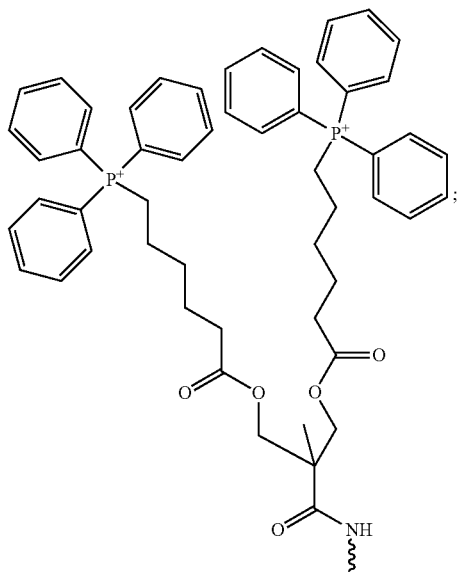

V

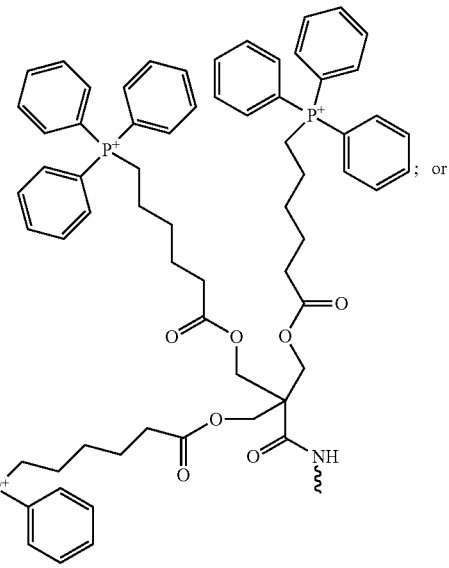

VI

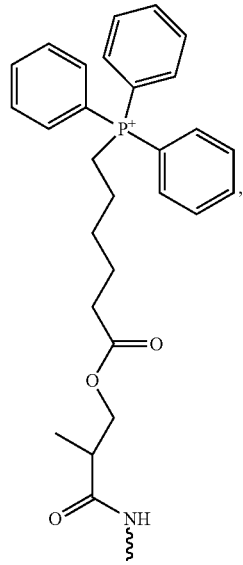

VII where the amine (as depicted) may be conjugated to a polymer, lipid, or the like for incorporation into the nanoparticle.

In embodiments, the delocalized lipophilic cation for targeting the mitochondrial matrix is a rhodamine cation, such as Rhodamine 123 having Formula VIII as depicted below:

VIII

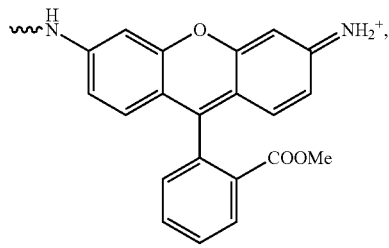

where the secondary amine (as depicted) may be conjugated to a polymer, lipid, or the like for incorporation into the nanoparticle.

Of course, non-cationic compounds may serve to target and accumulate in the mitochondrial matrix. By way of example, Szeto-Shiller peptide may serve to target and accumulate a nanoparticle in the mitochondrial matrix. Any suitable Szetto-Shiller peptide may be employed as a mitochondrial matrix targeting moiety. Non-limiting examples of suitable Szeto-Shiller peptides include SS-02 and SS-31, having Formula IX and Formula X, respectively, as depicted below:

IX

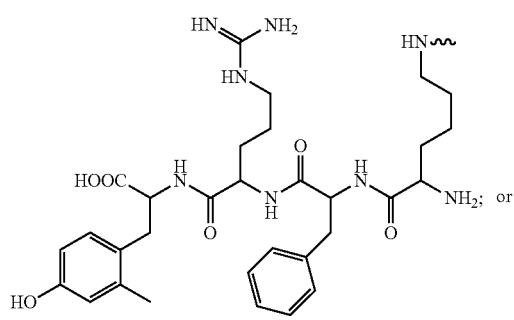

X

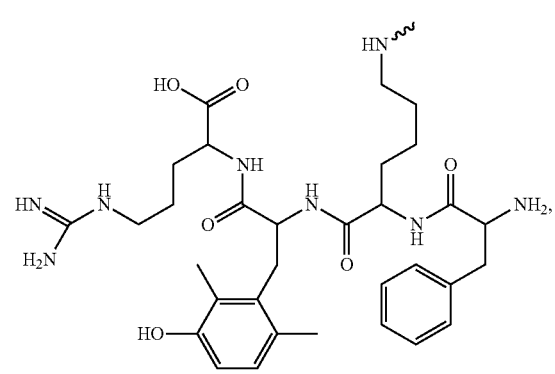

where the secondary amine (as depicted) may be conjugated to a polymer, lipid, or the like for incorporation into the nanoparticle.

For purposes of example, a reaction scheme for synthesis of distearoyl-snglycero-3-phosphoethanolamine (DSPE)-PEG-TPP is shown below in Scheme I. It will be understood that other schemes may be employed to synthesize DSPE-PEG-TPP and that similar reaction schemes may be employed to tether other mitochondrial targeting moieties to DSPE-PEG or to tether moieties to other polymers, copolymers, or lipids.

Scheme I.

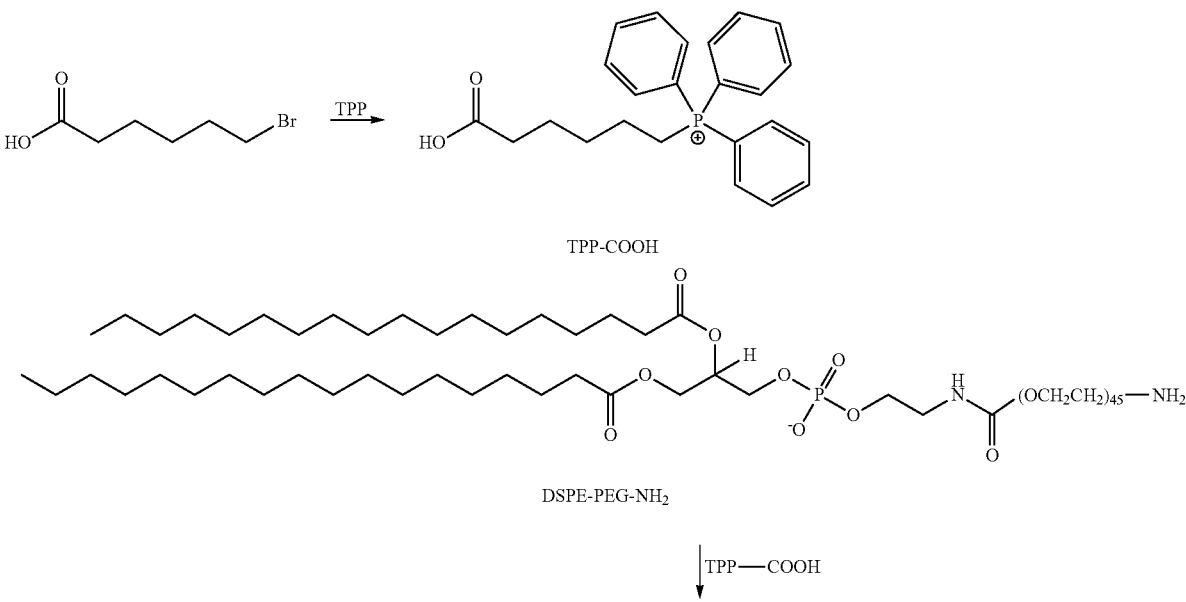

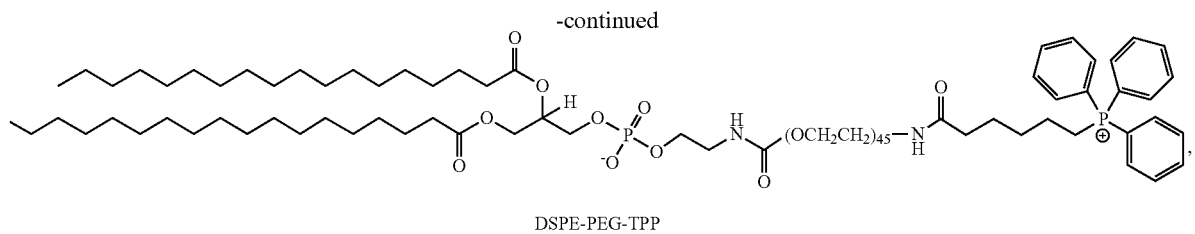

DSPE-PEG-TPP

C. Moieties for Targeting Macrophages

To increase the affinity of a nanoparticle for macrophage cells, which are characteristic of atherosclerosis lesions, mannose or other simple sugar moieties may be incorporated into the nanoparticle. Simple sugars, such as mannose and galactose, may selectively interact with macrophages through receptors. For example, macrophages contain macrophage mannose receptors and lectins that selectively bind galactose (macrophage galactose-binding lectin). Through these selective interactions, the presence of such simple sugars or compounds that include such simple sugars may be used to target the nanoparticles to macrophages. In embodiments, a macrophage targeting moiety includes mannose, galactose or lactobionic acid.

Because the presence of the simple sugars facilitates interactions of the nanoparticle with macrophages, the sugar moieties are preferable shielded in the nanoparticle until the nanoparticle reaches the desired location, such as an atherosclerotic plaque, to minimize exposure to the reticuloendothelial system (RES).

The sugar moieties may be temporarily shielded in any suitable manner. In embodiments, the sugar moieties are shielded by a hydrophilic polymer, such as polyethylene glycol (PEG); a hydrophilic portion of a polymer, such as a block copolymer containing a PEG block; a hydrophilic polymer bound to a lipid that is bound to the core or is part of a compound that, at least in part, forms the core; or the like. The shielding polymer may form a portion of the core of the nanoparticle (e.g., when the polymer is a block co-polymer and a hydrophobic block of the polymer contributes to formation of the core) or may be otherwise bound to the core.

Preferably, the shielding polymer is releasable from the nanoparticle when the nanoparticle reaches its target location, such as an atherosclerotic plaque, to expose the macrophage-targeting moiety. For example, the shielding polymer may be bound to the core, a polymer, a lipid, or the like via a cleavable linker. The cleavable linker may be cleaved when reaching the target location. Any suitable cleavable linker may be employed. In embodiments, the cleavable linker is a peptide linker cleavable by a matrix metalloproteinase (MMP). One example of a peptide linker cleavable by MMP2 is a polypeptide having the amino acid sequence GPLGVRG (SEQ ID NO:4). Regardless of the linker employed, cleavage preferably takes place at cleavage enzyme (such as MMP) concentrations at or below those present in atherosclerotic plaques. In embodiments, cleavage of the cleavable linker induces surface switching that results in exposure of the macrophage-targeting moiety.

Other cleavable linkers that may be employed are those susceptible to cleavage by glutathione, pH changes, temperature changes, or the like.

Non-limiting examples of macrophage targeting moieties bound to polymers, lipids, or the like include mannose, galactose, or lactobionic acid bound to short hydrophilic polymer chains, such as $PEG_{500}$. In embodiments, the short hydrophilic polymer chains are bound to the core via a lipid or hydrophilic polymer. For example, $PEG_{500}$ may be bound to a hydrophobic polymer, such as PLGA, which forms at part of the core. In embodiments, the short hydrophilic polymers are bound to a lipid, such as distearoyl-snglycero-3-phosphoethanolamine (DSPE), which is bound to the core or to a hydrophilic polymer forming part of the core. Larger hydrophilic chains, such as $PEG_{3400}$, may serve as shielding polymers. The shielding polymers may be bound to the core via a hydrophobic polymer, lipid or the like. The shielding polymers may be bound to the hydrophobic polymer, lipid, or the like via a cleavable linker.

In embodiments, the macrophage targeting moieties are bound to PEG, such as $PEG_{500}$, which is bound to PLGA (i.e., PLGA-PEG-targeting moiety). In embodiments, the macrophage targeting moieties are bound to PEG, such as $PEG_{500}$, which is bound to DSPE (i.e., DSPE-PEG-targeting moiety).

In embodiments the shielding polymer, such as $PEG_{3400}$, is bound to PLGA (i.e., PLGA-PEG) and may be bound to PLGA via a cleavable linker (i.e., PLGA-linker-PEG). In embodiments, the shielding polymer, such as $PEG_{3400}$, is bound to DSPE (i.e., DSPE-PEG) and may be bound to DSPE via a cleavable linker (i.e., DSPE-linker-PEG).

The macrophage-targeting moieties may be bound to the polymers or lipids in any suitable manner. By way of example, DSPE-PEG-mannose may be synthesized through amide coupling of D-mannosamine hydrochloride with DSPE-PEG-COOH; e.g., as shown in the following reaction scheme:

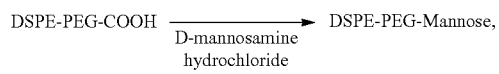

Scheme III.

where EDC is 1-ethyl-3-(3-(dimethylamino)-propyl)carbodiimide.

DSPE-PEG-lactobionic acid may be synthesized according to the following reaction scheme:

Scheme III.

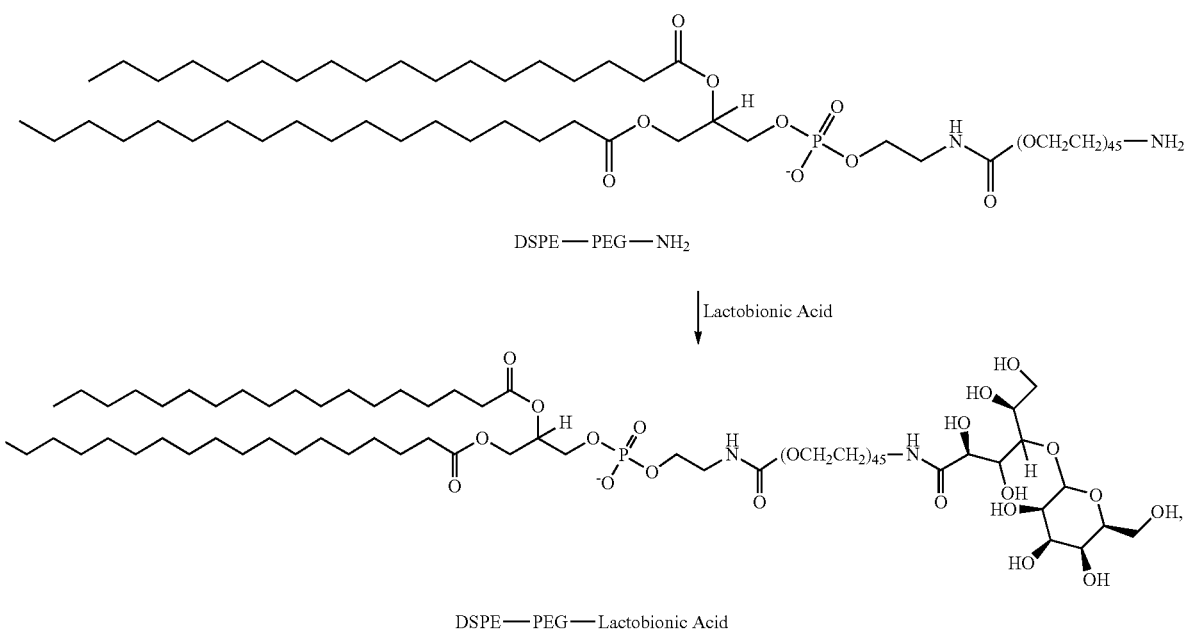

DSPE—PEG—Lactobionic Acid

It will be understood that the reaction schemes shown in Schemes II and III are for purposes of illustration and that other reaction schemes may be employed, as well as other phospholipids, polymers, or mannose or galactose containing compounds.

III. Phospholipid Monolayer

In embodiments the nanoparticle includes a phospholipid monolayer, which may be present at the interface of the hydrophobic core of the nanoparticle and the hydrophilic shell. The phospholipids of the monolayer have hydrophobic tails that interact with the hydrophobic core of the nanoparticle. The phospholipids may thus be used to tether various components, such as targeting moieties or contrast agents, to the core. The lipid layer may also serve to prevent agents in the core from freely diffusing out of the core and may reduce water penetration into the core.

Any suitable lipid or phospholipid may be employed. Examples of lipids or phospholipids that may be employed include lecithin, DSPE of different chain lengths, DSPE containing branched PEG, or the like. Preferably, the lipids are biodegradable. In embodiments, a lipid used to form a phospholipid monolayer is distearoyl-snglycero-3-phosphoethanolamine (DSPE).

As discussed above, the lipids may be used to tether various components to the core. In embodiments, the tethered components are further tethered by intervening polymers, preferably hydrophilic polymers such as PEG. The lipids may include reactive groups, or may be modified to contain reactive groups, for reaction with and binding to various polymers (which have or may be modified to have appropriate reaction groups) or other components (which have or may be modified to have appropriate reaction groups).

Examples of lipid-based tethered molecules include DSPE-PEG-lactobionic acid, DSPE-PEG-mannose, and DSPE-PEG-TPP discussed above. It will be understood that other phospholipids and hydrophilic polymers (other than DSPE and PEG) may be employed. It will be further understood that moieties such as DPA, PS-binding polypeptides, and the like may be tethered to a phospholipid, with or without an in intervening hydrophilic polymer, in a similar manner.

IV. HDL Components

In embodiments, the nanoparticle includes HDL or HDL-mimicking components.

HDLs oppose atherosclerosis directly, by removing cholesterol from foam cells, by inhibiting the oxidation of low-density lipoproteins (LDLs), and by limiting the inflammatory processes that underlie atherosclerosis. HDLs also have anti-thrombogenic properties. Thus, HDL-cholesterol (HDL-C) interrupts the process of atherogenesis at several key stages. Along with apoE, which promotes cholesterol efflux from foam cells, apoA-1 containing HDL is thought to facilitate the transport of cholesterol from lesions. Accordingly, incorporating HDL components and associated components, such as apoA-1 protein or a synthetic mimetic thereof, into a nanoparticle that targets atherosclerotic lesions may provide significant benefits to patients with ATVD or CHD.

In embodiments, an HDL component incorporated into the nanoparticle is cholesterol, such as cholesteryl oleate, reconstituted HDL from human plasma, or the like. In embodiments, the cholesterol is incorporated into, or forms a part of, the hydrophobic core of the nanoparticle. In embodiments, the cholesterol may incorporate into phospholipid monolayer, if present in the nanoparticle.

ApoA-1 or any suitable apoA-1 peptide mimetic may be incorporated into the nanoparticle. One example of an apoA-1 peptide mimetic is a polypeptide having the amino acid sequence FAEKFKEAVKDYFAKFWD (SEQ ID NO:5). ApoA-1 or apoA-1 mimetics will tend to self-assemble into the nanoparticles, particularly if the nanoparticle includes a phospholipid monolayer, and thus need not be tethered to other components such as polymers or lipids. However, such polypeptides may be tethered to polymers or lipids.

In embodiments, a self-assembled apoA-1 peptide network and a colloidal phospholipid monolayer mimic plasma derived HDL.

V. Contrast Agents

A nanoparticle (NP) as described herein may include one or more contrast agents for purpose of imaging, visualization or diagnosis. Any suitable contrast agent may be employed. In embodiments, the contrast agent is suitable for in vivo magnetic resonance imaging (MRI), such as iron oxide (IO) nanocrystals. In embodiments, the contrast agent is suitable for ex vivo/in vivo optical imaging, such as quantum dot (QD) (fluorescence), cdots, pdots, or the like. In embodiments, the nanoparticle includes both contrast agents for MRI and agents for fluorescent optical imaging.

A single construct containing complementary imaging agents could be of enormous benefits for atherosclerosis. NPs with the ability to carry both fluorescent (QD) and MRI (IO) probes represent an unique platform, which can find wide preclinical applications in the study of inflammatory atherosclerosis, postinfarction healing, transplant rejection, and early aortic valve disease, to name a few. These contrast agents enable the attainment of both high imaging sensitivity from fluorescence and high spatial resolution from MRI, which also helps to compensate for the limited imaging depths of fluorescence imaging. A targeted single NP platform containing both fluorescence and MRI contrast agents to allow imaging of apoptotic macrophages in the vulnerable plaque could help open the door for many promising human applications, including imaging of micro thrombi associated with vulnerable coronary plaques.

As both QD and IO can be synthesized in the same size range and with similar capping ligands, the NP platform will be uniform and can allow facile exchange of the components without significantly altering the overall properties of the NP. The localized regions of higher fluorescence signal seen ex vivo using this platform may be useful for correlating with vulnerable plaques identified in vivo by MRI.

Contrast agents may be incorporated into the NP in any suitable manner. In embodiments, the contrast agents are incorporated into the core or are contained within the core. In embodiments, the contrast agents are tethered to a lipid, polymer, protein or other component of the nanoparticle. Such tethering can be carried out as described above with regard to other components of the nanoparticle, such as targeting moieties.

By way of example, as described herein QD has been conjugated to PEG to form QD-conjugated amine-terminated PEG ($NH_2$-PEG-QD) that was conjugated to PLGA-COOH to produce PLGA-b-PEG-QD.

Contrast agents may be present in a nanoparticle in any suitable amount. In embodiments, a contrast agent is present in a nanoparticle from about 0.05% by weight to about 20% by weight of the nanoparticle.

VI. Therapeutic Agents

A nanoparticle, as described herein, may include any one or more therapeutic agent.

The therapeutic agent may be embedded in, or contained within, the core of the nanoparticle. Preferably, the therapeutic agent is released from the core at a desired rate. If the core is formed from a well-known and well-studied polymer (such as PLGA) or combination of polymers, the release rate can be readily controlled.

In embodiments, a therapeutic agent or precursor thereof is conjugated to a polymer, lipid, etc., in a manner described above with regard to targeting moieties. The therapeutic agent may be conjugated via a cleavable linker so that the agent may be released when the nanoparticle reaches the target location, such as an apoptotic macrophage.

The therapeutic agents may be present in the nanoparticle at any suitable concentration. For example, a therapeutic agent may be present in the nanoparticle at a concentration from about 0.01% to about 20% by weight of the nanoparticle.

In embodiments, the nanoparticle includes one or more therapeutic agent useful for treatment of vascular plaques, ATVD, or CHD. For example, a nanoparticle may include one or more statin, one or more fibrate, or combinations thereof. Suitable statins include atorvastin, simvastatin, and lovastatin. Suitable fibrates include bezafibrate, fenofibrate, and gemfibrizol. In embodiments, atorvastatin is present in combination with one or more of simvastatin, lovastatin, bezafibrate, fenofibrate, or gemfibrizol.

In embodiments, a nanoparticle includes chenodeoxylcholic acid or another repressor (e.g., siRNA) of PCSK9. Repression of PCSK9 promotes hepatic LDL receptor degradation, and may enhance efficacy of statins or fibrates when used in combination.

VII. Size of Nanoparticle

Nanoparticles, as described herein, may be of any suitable size. Generally, the nanoparticles are of a diametric dimension of less than about 999 nanometers, such as less than about 750 nm, less than about 600 nm, less than about 500 nm, less than about 400 nm, less than about 300 nm, or less than about 200 nm. In addition, or alternatively, the nanoparticles may be of a diametric dimension of greater than about 5 nm. In embodiments, the nanoparticles are from about 30 nm to about 300 nm in diameter. In embodiments, the nanoparticles are separated according to size, such as from about 20 nm to about 40 nm, from about 40 nm to about 60 nm, from about 60 nm to about 80 nm, from about 80 nm to about 100 nm, or from about 100 nm to about 150 nm.

The size of the nanoparticle is one factor that may influence bio-distribution and mitochondrial uptake, if appropriate.

VIII. Synthesis of Nanoparticle

Nanoparticles, as described herein, may be synthesized or assembled via any suitable process. Preferably, the nanoparticles are assembled in a single step to minimize process variation. A single step process may include nanoprecipitation and self-assembly.

In general, the nanoparticles may be synthesized or assembled by dissolving or suspending hydrophobic components in an organic solvent, preferably a solvent that is miscible in an aqueous solvent used for precipitation. In embodiments, acetonitrile is used as the organic solvent, but any suitable solvent may be used. Hydrophilic components are dissolved in a suitable aqueous solvent, such as water, 4 wt-% ethanol, or the like. The organic phase solution may be added drop wise to the aqueous phase solution to nanoprecipitate the hydrophobic components and allow self-assembly of the nanoparticle in the aqueous solvent.

A process for determining appropriate conditions for forming the nanoparticles may be as follows. Briefly, functionalized polymers and phospholipids may be co-dissolved in organic solvent mixtures (in embodiments, the phospholipids or functionalized phospholipids are dissolved in the aqueous solvent). This solution may be added drop wise into hot (e.g, 65° C.) aqueous solvent (e.g, water, 4 wt-% ethanol, etc.), whereupon the solvents will evaporate, producing nanoparticles with a hydrophobic core coated with phospholipids. The phospholipids used at this stage may be a mixture of non-functionalized phospholipids and functionalized phospholipids (e.g., conjugated to targeting moieties) than may also include a hydrophilic polymer component, such as PEG. Once a set of conditions where a high (e.g., >75%) level of targeting moiety surface loading has been achieved, contrast agents or therapeutic agents may be included in the nanoprecipitation and self-assembly of the nanoparticles.

If results are not desirably reproducible by manual mixing, microfluidic channels may be used.

Aqueous suspension of nanoparticles containing DPA moieties on the surface may be reacted with an aqueous solution of $Zn(NO_3)_2 \cdot 6H_2O$ for the formation of multiple $Zn^{2+}$-DPA PS binding sites on the NP surface. Contrast agent (such as IO or QD) and $Zn^{2+}$ loading in the NPs may be quantified by ICP-MS. Therapeutics loading and encapsulation efficiency (EE) may be determined by HPLC.

Resulting NPs may be tested and characterized for their physical characteristics. For example, the effect of MMP2 on the cleavage of the PEG chains may be established via particle size measurements. Preferably, cleavage is observed at MMP2 concentrations below those in atherosclerotic plaques. Libraries of NPs may be screened these for desired characteristics.

NPs may be characterized for their size, charge, stability, IO and QD loading, drug loading, drug release kinetics, surface morphology, and stability using well-known or published methods.

NP properties may be controlled by (a) controlling the composition of the polymer solution, and (b) controlling mixing conditions such as mixing time, temperature, and ratio of water to organic solvent. The likelihood of variation in NP properties increases with the number of processing steps required for synthesis.

The size of the nanoparticle produced can be varied by altering the ratio of hydrophobic core components to amphiphilic shell components. The choice of PEGylated lipids and bilayer forming phoshpholipds can affect resulting nanoparticle size. PEGylated lipids are known to form small micellar structures because of surface tension imposed by the PEG chains. NP size can also be controlled by changing the polymer length, by changing the mixing time, and by adjusting the ratio of organic to the phase. Prior experience with NPs from PLGA-b-PEG of different lengths suggests that NP size will increase from a minimum of about 20 nm for short polymers (e.g. $PLGA_{3000}$-$PEG_{750}$) to a maximum of about 150 nm for long polymers (e.g. $PLGA_{100,000}$-$PEG_{10,000}$). Thus, molecular weight of the polymer will serve to adjust the size.

NP surface charge can be controlled by mixing polymers with appropriately charged end groups. Additionally, the composition and surface chemistry can be controlled by mixing polymers with different hydrophilic polymer lengths, branched hydrophilic polymers, or by adding hydrophobic polymers.

Once formed, the nanoparticles may be collected and washed via centrifugation, centrifugal ultrafiltration, or the like. If aggregation occurs, NPs can be purified by dialysis, can be purified by longer centrifugation at slower speeds, can be purified with the use surfactant, or the like.

Once collected, any remaining solvent may be removed and the particles may be dried, which should aid in minimizing any premature breakdown or release of components. The NPs may be freeze dried with the use of bulking agents such as mannitol, or otherwise prepared for storage prior to use.

Figure 1B:
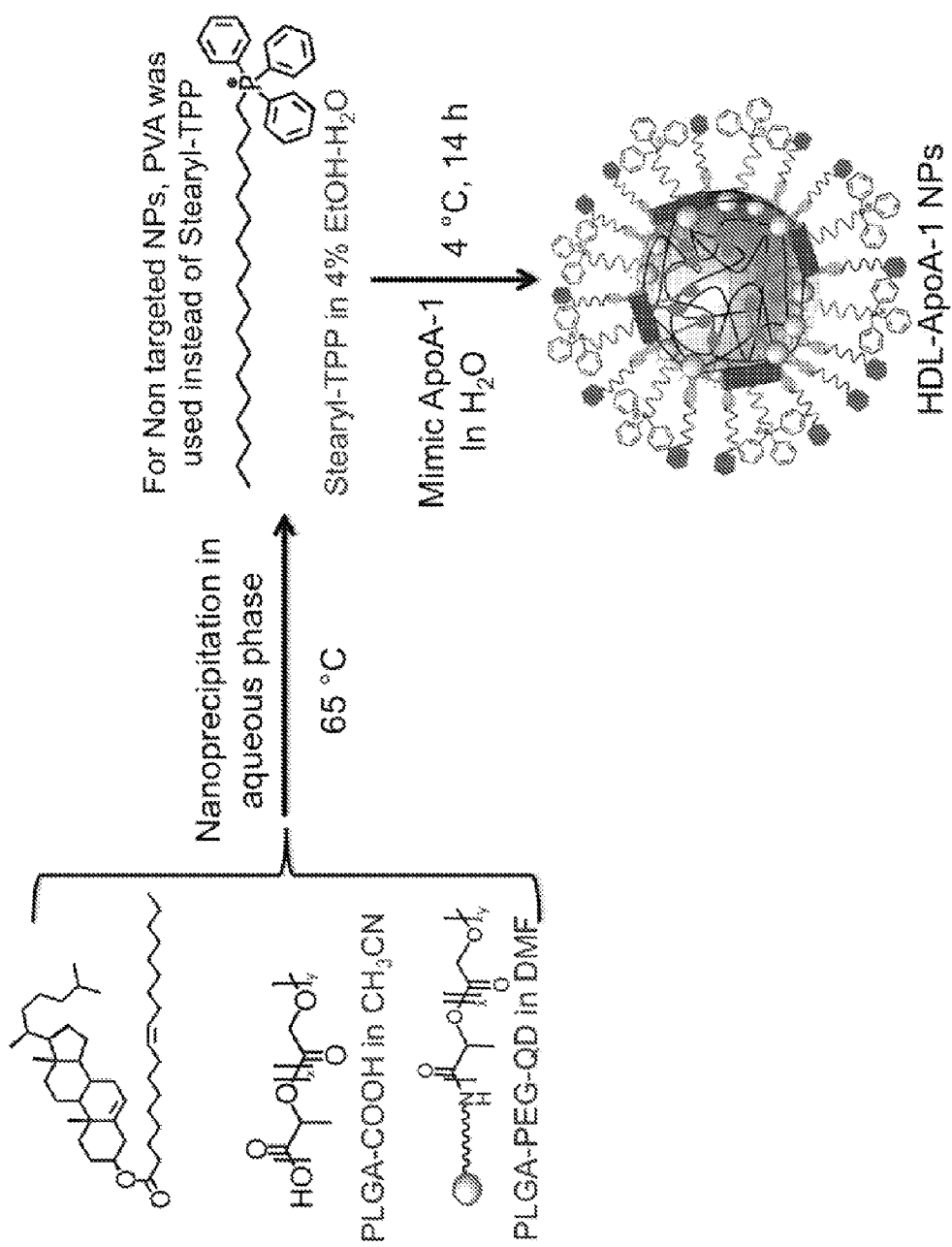
FIG. 1B is an overview of an embodiment of a reaction scheme for HDL-mimicking nanoparticles by nano-precipitation.

For purposes of illustration, an example of a reaction scheme that may be employed for nanoprecipitation and self-assembly of a macrophage, mitochondrial matrix-targeted HDL mimicking polymer lipid hybrid is depicted in the reaction scheme shown in FIG. 1A. As depicted, the organic phase, which contains cholesteryl oleate, PLGA and PLGA-PEG-QD is nanoprecipitated in the aqueous phase, which contains DSPE-PEG-TPP, DSPE-Lactobionic Acid, and apoA-I peptide mimetic, the resulting mixture is vortexed, stirred and the nanoparticles are allowed to self-assemble. FIG. 1B provides additional detail regarding the reaction scheme. The aqueous phase may be heated and the organic phase may be added to the aqueous phase in drop wise fashion under gentle stirring. The resulting mixture may be vortexed for any suitable time, such as about 3 minutes, and gentle stirring at, for example, room temperature may occur for a suitable time (e.g., about 2 hours) to allow for self-assembly. Solvent and free molecules may be removed by any suitable process, such as washing and use of a centrifugal filter with an appropriate molecular weight cut off (e.g., about 10000 Da).

The organic phase components may be present in the organic solvent, such as acetonitrile, at any suitable concentration, such as from about 1 mg/ml to about 5 mg/ml. The aqueous phase components may be present in the aqueous solvent, such as 4 wt-% ethanol, at any suitable concentration. Following nanoprecipitation of the organic phase, the apoA-1 peptide may be present at a weight ratio of 15% relative to the PLGA polymer.

While not shown, it will be understood that therapeutic agents may be placed in the organic phase or aqueous phase according to their solubility. For example, most statins or fibrates may be dissolved in the organic phase. Chenodeoxyxholic acid can be dissolved in aqueous phase.

Figure 2A:
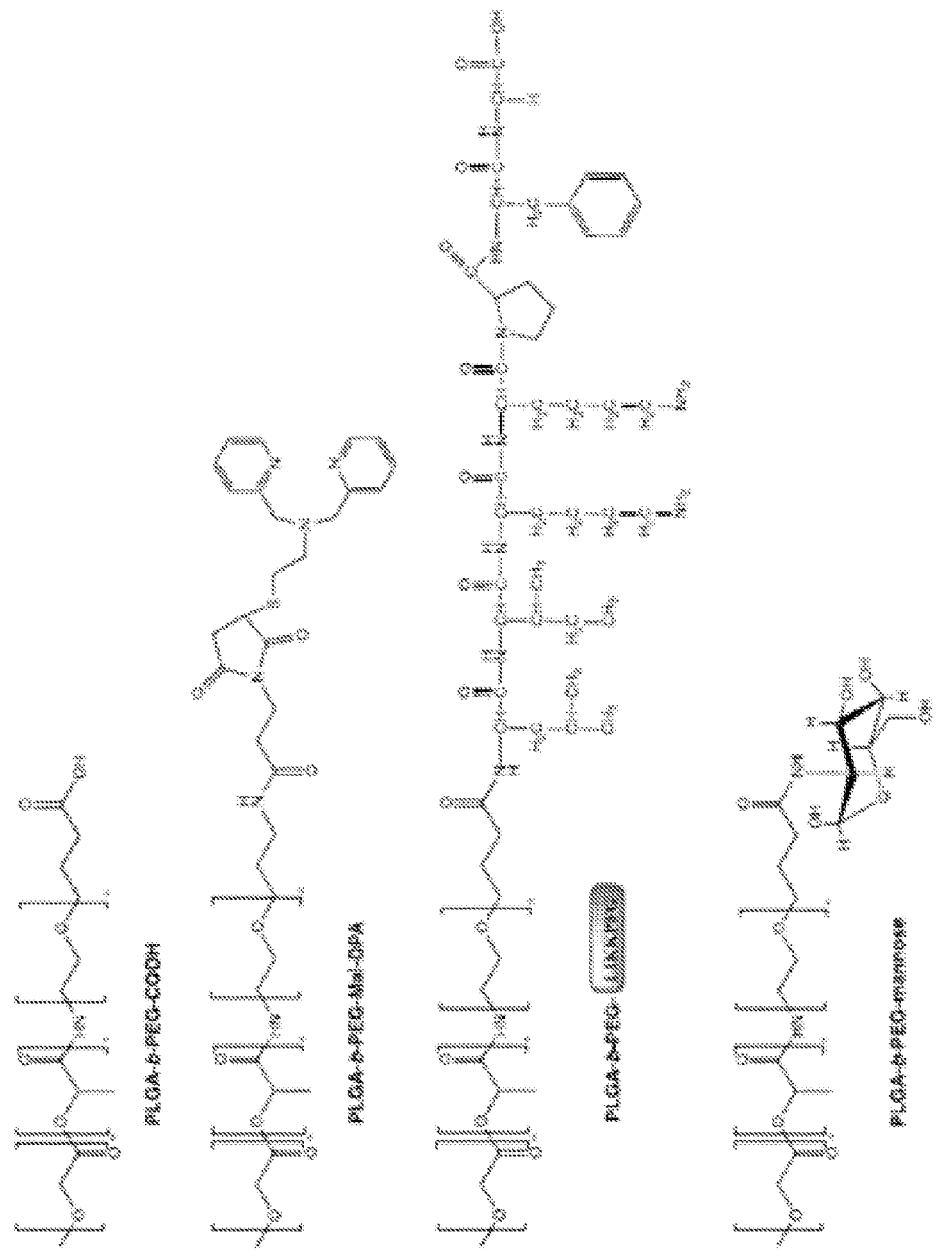
FIGS. 2A-B are an overview of an embodiment of a reaction scheme for blended nano-precipitation of a nano-sensor for atherosclerotic plaques.
Figure 2B:
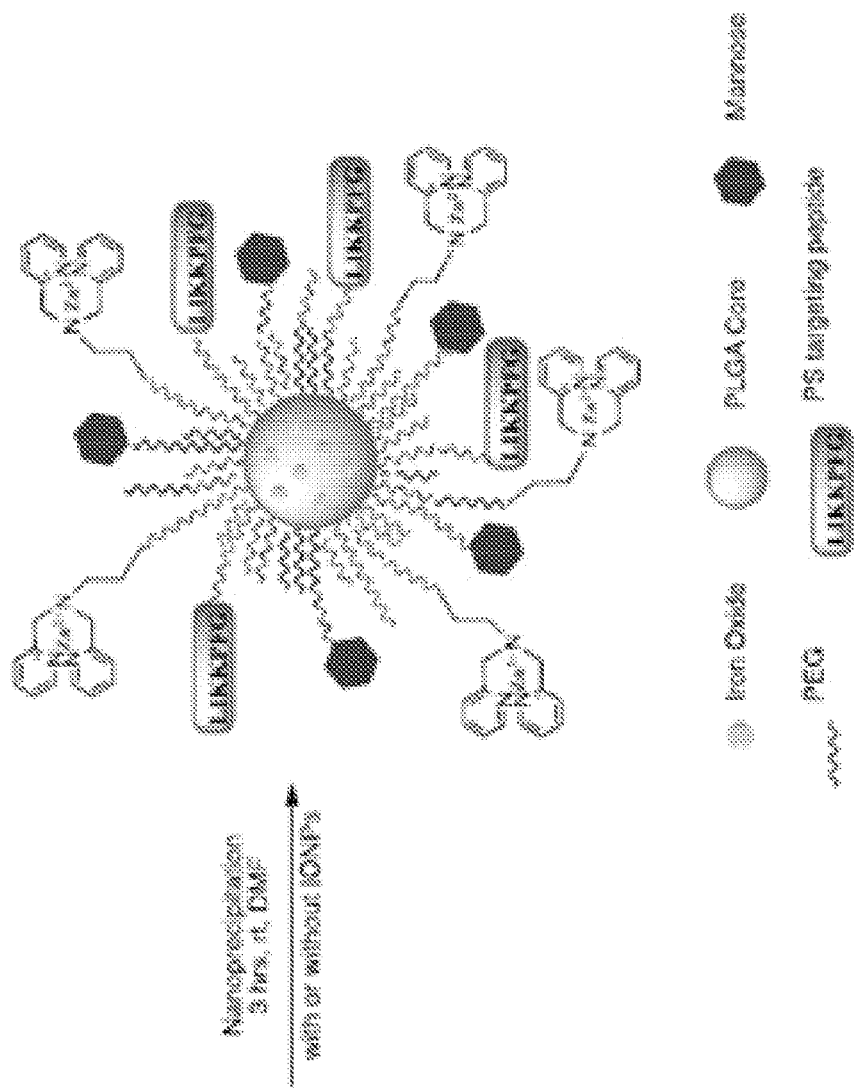

FIGS. 2A-B illustrate another reaction scheme for preparing an embodiment of a nanoparticle. In the depicted reaction scheme PLGA-b-PEG-COOH, PLGA-b-PEG-Mal-DPA, PLGA-b-PEG-LIKKPFG, and PLGA-b-PEG-mannose may be dissolved in an organic solvent, such as DMF, and nanoprecipitated in an aqueous solvent and allowed to self-assemble into nanoparticles schematically represented in FIG. 2B.

It will be understood that the reaction scheme and components depicted in FIGS. 1A-B and 2A-2B are only for purposes of illustration and not limitation. It will be understood that other components and reaction schemes may be employed to produce a nanoparticle as described herein.

As indicated in the provisional application to which the present application claims priority, in embodiments the NP core includes a PLGA matrix, and the core is coated with functionalized polyethylene glycol (PEG) chains. Conjugated PLGA-b-PEG block copolymer was chosen for its controlled biodegradability, safety, and compatibility in biological systems. Multifunctional PEG also allows for the conjugation and binding of targeting moieties for apoptosis in atherosclerotic plaques. Initially, synthesis of the NP was accomplished by attaching the targeting ligands to the block copolymer, or by attaching the ligands to heterofunctional PEG chains and then conjugating to PLGA. Reagents used in conjugations include but are not limited to: 1-Propanephosphonic acid cycle anhydride (T3P), N-Hydroxysuccinimide, and 1-ethyl-3-(3-dimethylaminopropyl) carbodiimide) (EDC) (Table 1).

TABLE 1

Common polymer to ligand conjugations attempted.

| Polymer | | Targeting Moiety |
|---|---|---|
| PLGA-COOH | + | NH2-PEG-COOH |
| PLGA-PEG-Maleimide | + | Dipicolylamine ligand |
| PLGA-PEG-COOH | + | LIKKPFG peptide |
| PLGA-PEG-COOH | + | Glucosamine |

Combinations of the functionalized PLGA-b-PEG polymers were combined to produce polymeric nanoparticles by a blended precipitation method. Nanoprecipitation was accomplished by dissolving polymer in organic solvents at various mg/mL concentrations, and the polymer solution was added dropwise to water, with or without the encapsulation of a fluorophore or an MRI contrast agent. Solvents utilized in nanoprecipitation include: N,N-dimethylformamamide (DMF), acetonitrile (ACN), among others. Nanoprecipitation blended multiple compositions of the functionalized polymers by weight, and further optimization of nanoparticle size and targeting abilities may be carried out by adjusting percent compositions.

As an alternative to blended nanoprecipitation methods, a PLGA core may be coated with a surface-switching lipid polyethylene glycol conjugate that ensures long circulating properties. Hybrid nanoparticle synthesis includes phospholipids and 1,2-distearoyl-snglycero-3-phosphoethanolamine-N-carboxy to polyethylene glycol (DSPE-PEG) dissolved in organic solvents. The PLGA, hydrophobic phospholipids, and DSPE-PEG chains will self-assemble into NPs. Incorporating DSPE-PEG in the phospholipid monolayer stabilizes the NP platform and provides for a longer in vivo circulation. Additionally, the carboxylic ends of the DSPE-PEG chains allow for the binding of apoptosis targeting moieties. The PS-sensing and macrophage-targeting ligands may be conjugated directly to the NP surface. Adjusting the concentrations of PLGA and PEG will vary the size and number of PEG chains. The quantity of functionalized ligands added to the surface may be optimized. A technique involving microfluidic rapid mixing may also be used for producing PLGA-PEG NPs. A construct composed of ligand-functionalized gold nanoparticles surrounding a polymeric nanoparticle may also be used for the detection of and potential drug delivery vehicle for atherosclerotic plaques.

To enable visualization of NP accumulation with clinical imaging modalities, the PLGA core may incorporate either a fluorophore or iron oxide nanocrystals, for fluorescence or magnetic resonance imaging, respectively. The inclusion of imaging agents may be accomplished through similar self-assembly methods. Confocal imaging of the fluorophore encapsulation may be taken to optimize loading. After sufficient loading has been confirmed, iron oxide nanocrystals from variable concentrations synthesized from literature methods may be encapsulated. The IO concentration may be varied to achieve suitable loading efficiency for MRI. Human and murine macrophage cell lines may be used, with and without chemical induction of apoptosis, to assess the PS sensing ability of the NP construct.

IX. Use and Testing

In general, a nanoparticle as described herein may be targeted to apoptotic cells or be useful for monitoring apoptosis of cells. Preferably, the nanoparticle targets macrophages within atherosclerotic plaques. However, the nanoparticles may target other apoptotic cells, such as cancer cells.

The nanoparticles may be used for visualization, imaging, monitoring, diagnosis, or treating apoptotic cell populations. For example, the nanoparticles may be used for visualization, imaging, monitoring, diagnosis, or treating atherosclerotic plaques or diseases associated therewith, such as ATVD or CHD.

The performance and characteristics of nanoparticles produced herein may be tested or studied in any suitable manner. By way of example, therapeutic efficacy can be evaluated using cell-based cholesterol lowering assays. Toxicity, bio-distribution, pharmacokinetics, and efficacy studies can be tested in rodents or other mammals. Zebrafish models may be employed for combined imaging and therapy studies. Atherosclerotic rabbits and pigs may be used to further evaluate diagnostic or therapeutic potential of nanoparticles. Some additional details of studies that may be performed to evaluate the performance or characteristics of the nanoparticles, which may be used for purposes of optimizing the properties of the nanoparticles are described below. However, one of skill in the art will that other assays and procedures may be readily performed.

Uptake and binding characteristics of nanoparticles (NPs) encapsulating fluorescent QD will be evaluated in any suitable cell line, such as RAW 264.7, J774, jurkat, and HUVEGs cells. The immunomodulatory role of NPS may be assayed by determining the release of cytokines when these cells are exposed to varying concentrations of NPs. Complement activation may be studied to identify which pathways are triggered using columns to isolate opsonized NPs; e.g. as described in Salvador-Morales C, Zhang L, Langer R, Farokhzad O C, Immunocompatibility properties of lipid-polymer hybrid nanoparticles with heterogeneous surface functional groups, *Biomaterials* 30: 2231-2240, (2009). Fluorescence measurements may be carried out using a plate reader, FACS, or the like. Because NP size is an important factor that determines biodistribution, NPs may be binned into various sizes (e.g., 20-40, 40-60, 60-80, 80-100, 100-150, and 150-300 nm) and tested according to size.

Smooth muscle cells (SMCs), macrophages, and endothelial cells are major cell types of interest in atherosclerotic plaques. The uptake of NPs with and without MMP2 in these cell types may be evaluated via high throughput fluorescence imaging techniques. If the nanoparticles include a shielding polypeptide having a MMP2 cleavable linker that protects a macrophage binding moiety (e.g., mannose, galactose, lactobionic acid), it is anticipated that only in the case where the NPs are incubated with macrophages and MMP2, receptor-mediated uptake of NPs will be observed. The results of such uptake experiments may be confirmed using MRI imaging of pellets of cells incubated under MMP2 and control situations. MRI measurements of cell pellets may be performed at 7 T systems using a 38 mm transmit and receive 1H quadrature coil. A set of 4-6 cell vials may be placed in an MRI system with agarose phantom as a background signal. A single slice T2*, T2, and T1 images of the cell vials of different concentrations may be obtained. T2* weighting may be achieved using a single-slice multi-gradient echo sequence. Quantitative T2 measurement may be performed using a Carr-Purcell-Meiboom-Gill sequence. From these measurements, r1, r2 and r2* relaxivites may be calculated. These ex-vivo measurements may be used to aid in determining optimum concentration, imaging sequence, and parameters for in vivo imaging. For apoptosis detection, Jurket cell may be used. For both MRI and FL imaging, cells may be treated with etoposide for induction of apoptosis. Annexin-V may be used as a control. In addition, selectivity towards apoptotic over necrotic cell may be evaluated via staining with the DNA intercalator 7-aminoactinomycin D (7-AAD), which enters necrotic cells.

The effect of therapeutic agents such as statins, fibrates, or combinations thereof in NP formulations may be examined on macrophage-derived foam cells formed by oxidized LDL (oxLDL) which is a hallmark of early atherogenesis. RAW 264.7 macrophages may be treated with various doses of oxLDL for foam cell formation which can be followed by Oil Red O staining After foam cell formations, these cells may be treated with targeted NPs containing therapeutic agents. Cellular lipids may be obtained by sonicating the cells in hexane/isopropanol (3/2, v/v) and extracting for 24 h. After removing cell debris by centrifugation, the supernatant may be dried under nitrogen flush and re-dissolved in isopropanol. Total cholesterol can be determined with an Amplex Red Cholesterol Assay Kit.

To conduct an extensive combined imaging and therapy study where NPs include IO-QD and therapeutic agent, such as statin, a zebrafish model may be employed, preferably after in vitro testing and optimization using cell culture systems. Imaging and therapeutic efficacy of lead NPs may be assessed in zebrafish to eliminate problematic formulations early in development. Efficacy of statin combination and imaging ability of NP constructs may be evaluated in high-cholesterol diet (HCD)-fed zebrafish larvae. An advantage of using zebrafish is that their larvae are optically transparent until about the $30^{th}$ day of development, which enables temporal observations of fluorescent probes in a live animal. Hypercholesterolemia and lipoprotein oxidation achieved in zebrafish and characteristics of vascular lipid accumulation in inflammatory processes, relevant to human atherogenesis, make the zebrafish model an attractive in vivo system. The ability of NPs to reduce cholesterol levels in HCD-fed zebrafish larvae may be studies. Wild-type (AB) zebrafish embryos may be obtained by in vitro fertilization and natural spawning of adults maintained at 28° C. on a 14/10 h light/dark cycle. Zebrafish larvae may be fed twice a day with either control diet or HCD. Zebrafish larvae may be injected i.v. with NPs. After the treatment period imaging may be performed using a confocal microscope. Zebrafish larvae may be euthanized by exposure to 0.05% tricaine, abdomens containing undigested food may be removed, and the remaining bodies may be pooled and gently homogenized. Total lipid extraction may be performed with 1:2 methanol/dichloromethane. Cholesterol esters may be saponified and total cholesterol may be measured. Student's t-test or other appropriate statistical analysis may be used to analyze differences between means of 2 groups.

Biodistribution (bioD) and pharmacokinetic (PK) studies may be carried out in rats or other suitable mammals. For PK and bioD analysis, Sprague Dawley rats may be dosed with QD-labeled, apoptosis-targeting, macrophage-targeting NPs or similar NPs without the targeting groups, through a lateral tail vein injection. The bioD may be followed initially by fluorescence imaging for 1-24 h after injection. Animals may be sacrificed; and brain, heart, intestine, liver, spleen, kidney, muscle, bone, lung, lymph nodes, gut, and skin may be excised, weighed, homogenized, and Cd from QD may be quantified using ICP-MS. Tissue concentration may be expressed as % of injected dose per gram of tissue (% ID/g). Blood half-life may be calculated from blood Cd concentrations at various time points Combined imaging and therapy studies may be employed in atherosclerotic rabbits or pigs or other suitable animal model. NPs may be studies in a double balloon injury New Zealand white rabbit model of atherosclerosis. The NPs may be given at the FDA approved statin dose ranges, as typically used in patients. First, animals may be used to determine the half-life, bioD, and cellular localization. The circulation half-life of the NPs may be used to determine imaging time points. Post-injection imaging may be done at 5 times the circulation half-life, when signals from the blood has cleared. The organs of the animals may be harvested for bioD studies. 5 mm pieces may be cut from the aorta of each animal, embedded and sectioned. The resulting tissue sections may be imaged using confocal microscopy and TEM to investigate the distribution of the NPs in the aorta. The delivery of the NPs into the plaque may be evaluated using T2*-weighted MRI imaging and fluorescence (FL) imaging. Groups of animals may be used for each control NPs, and various NP formulations, free drug, saline, etc. These animals may be injected four times, once a week for four weeks. The animals may be imaged prior to therapy to establish baseline parameters. MR and FL imaging may be performed at the post-injection time point determined from the circulation half-life. Once the imaging study is completed, all the animals may be sacrificed and their aortas may be removed for histology, staining for SMCs, macrophages, and endothelial cells, allowing evaluation of the effects of the therapy.

Therapeutic dosages of nanoparticles effective for human use can be estimated from animal studies according to well-known techniques, such as surface area or weight based scaling.

In the following, non-limiting examples are presented, which describe various embodiments of representative nanoparticles, methods for producing the nanoparticles, and methods for using the nanoparticles.

EXAMPLES

Example 1

Synthesis of PLGA-b-PEG-Mal-DPA

A substituted DPA ligand, 2-(bis(pyridin-2-ylmethyl) amino)ethanethiol was synthesized and characterized by spectroscopic method. This DPA ligand was coupled to PEG using maleimide-PEG-NH2 to give NH2-PEG-Mal-DPA, which was coupled to PLGACOOH to give PLGA-b-PEG-Mal-DPA for $Zn^{2+}$ coordination. Synthesis was characterized by NMR, MALDI-TOF measurements and purity was confirmed by gel permeation chromatography (GPC).

Example 2

Synthesis of PLGA-b-PEG-LIKKPF

LIKKPF (SEQ ID NO:1) was synthesized using an automated peptide synthesizer at the Complex Carbohydrate Research Center, UGA. The peptide was purified by liquid chromatography methods and analyzed by Matrix Assisted Laser Desorption Ionization (MALDI) mass spectrometry. The amino acid monomers of leucine, isoleucine, lysine, lysine, proline, and phenylalanine were added by peptide coupling reagents to a glycine (G) based resin.

PLGA-PEG-COOH (0.0377 g, 1.08-0.627 µmoles) was dissolved in dichloromethane with 0.0025 g (0.617 mmoles) EDC and 0.0030 g (0.617 mmoles) sulfo NHS. The mixture was stirred for 2 h, and the PLGA-PEG-NHS ester was precipitated with ice cold diethyl ether. The product was washed twice and centrifuged for 10 min at 4000 rpm and −10° C. The pellet was dried for 30 min and added to the deprotected peptide in the presence of 6 µL DIEA in Dichloromethane (scheme 5). The mixture stirred overnight. The conjugated polymer-peptide was precipitated with ice cold diethyl ether by two washings, as above. The pellet was dried overnight. The polymer-peptide construct was redissolved in 1 mL of 50/50 (v/v) TFA/dichloromethane and stirred for 2 h with refreshing by dichloromethane. The sample was concentrated and washed with 6 mL of diethyl ether to get rid of the TFA and precipitate the polymer-peptide, respectively. The vial was dried, and mass of 0.0211 g was obtained, which represents a 95%-55% yield.

The resulting construct was characterized by NMR, MALDI-TOF measurements and purity was confirmed by gel permeation chromatography (GPC).

Example 3

Synthesis of DSPE-PEG-Mannose

The carbodiimide coupling of mannosamine to 1,2-distearoyl-sn-glycero-3-phosphoethanolamine-N-[carboxy (polyethylene glycol)-2000] (ammonium salt) (DSPE-PEG (2000)-COOH) was carried out according methods reported in literature. DSPE-PEG-COOH 103.8 mg (0.0364 mmole) was first micellized in 10 mL of 0.01 M PBS buffer. EDC (11.1 mg, 0.0579 mmole) and Sulf-NHS (11.7 mg, 0.543 mmole) were added to the DSPE in PBS, to yield a pH of 4.13. After 15 min of stirring, 15.3 mg (0.0710 mmole) of mannosamine hydrochloride was added (scheme 6). The pH of the mixture was increased to approximately 7.0 and maintained for 3 h. The mixture was dialyzed (MWCO 100-500 Dalton) against PBS at a pH of 7.34 overnight. The mixture was lyophilized to yield a white powder. The DSPE-PEG-mannose was dissolved in ethanol at 60° C. to remove any unreacted sugar or buffer salts. The ethanol was evaporated by rotovapping and by lyophilization. A white powder weighing 0.4362 g, to give a 24% yield.

The resulting construct was characterized by NMR, MALDI-TOF measurements and purity was confirmed by gel permeation chromatography (GPC).

Example 4

Synthesis of PLGA-b-PEG-QD

For QD encapsulation, a QD-conjugated amine-terminated PEG, NH2-PEG-QD, was conjugated to PLGA-COOH give a tri-block copolymer PLGA-b-PEG-QD using EDC/NHS amide coupling reaction. The product was characterized DLS measurements.

Example 5

Formation of Nanoparticles

In preliminary studies, varying IO and QD concentrations were encapsulated within
PLGA-b-PEG-NPs (for QD encapsulation, PLGA-b-PEG-QD prepared according to Example 4, was used) by blending PLGA-b-PEG-LIKKPF (prepared according to Example 2), PLGA-PEG-Mal-DPA (prepared according to Example 1) with PLGA-PEG-COOH using nanoprecipitation. To induce the polymers to self-assemble into nanoparticles, PLGA-PEG-Mal-DPA, PLGA-PEG-LIKKPF, and PLGA-PEG-QD were dissolved in acetonitrile. DSPE-PEG-Mannose in 4% ethanol-water was heated to 65° C. The polymer solution was added slowly at an approximate rate of 1 mL/min to the lipid mixture. The solution was stirred for two h. The nanoparticles were purified by using ultracentrifugation method and resuspended inn water. For $Zn^{2+}$ coordination, 10 µL of a $10^{-3}$ $Zn(NO_3)_2.6H_2O$ was added to the nanoparticles and incubated for approximately 30 min and purified by ultracentrifugation.

Example 6

Characterization of Nanoparticles

The size and zeta potential of each NP formulation was measured using dynamic light scattering (DLS). The surface morphology was studied using transmission electron microscopy (TEM). The resulting NPs had a size range of ~150 nm with ~4% QD, ~5% IO, and ~10% zinc loading as quantified by Inductively coupled plasma mass spectrometry (ICP-MS). With our initial success in synthesizing targeted FL/MRI active NPs with multiple functionalities on the surface.

Figure 3:
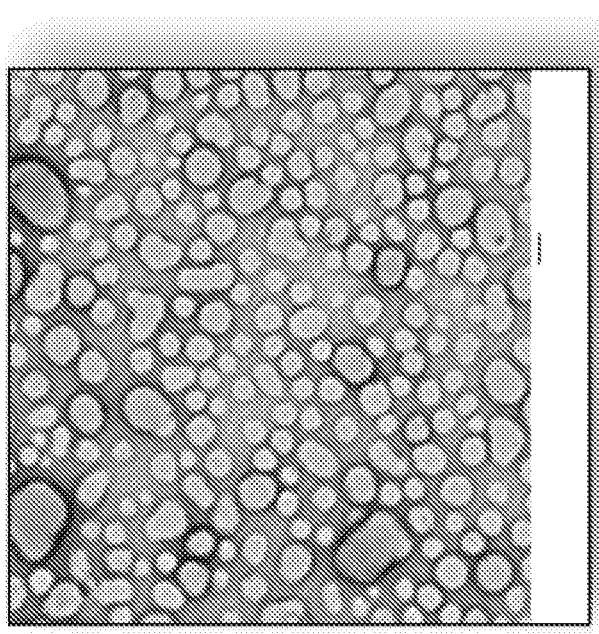
FIG. 3 presents transmission electron microscopy (TEM) images of nanoparticles formed as described herein.
Figure 3:
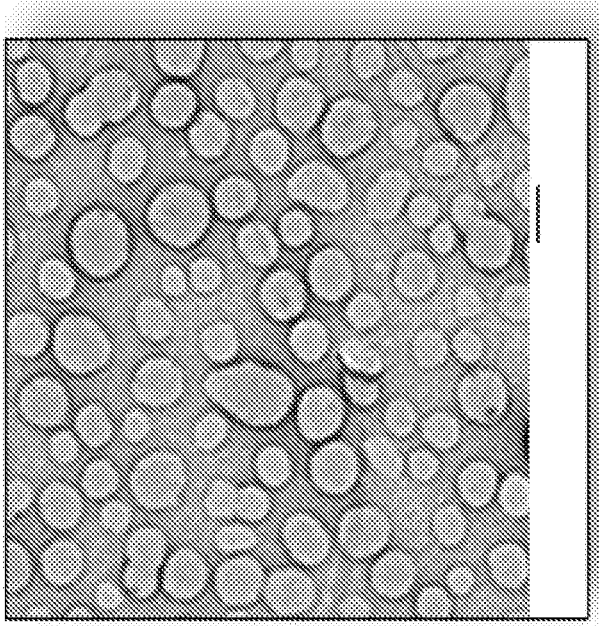
Figure 4:
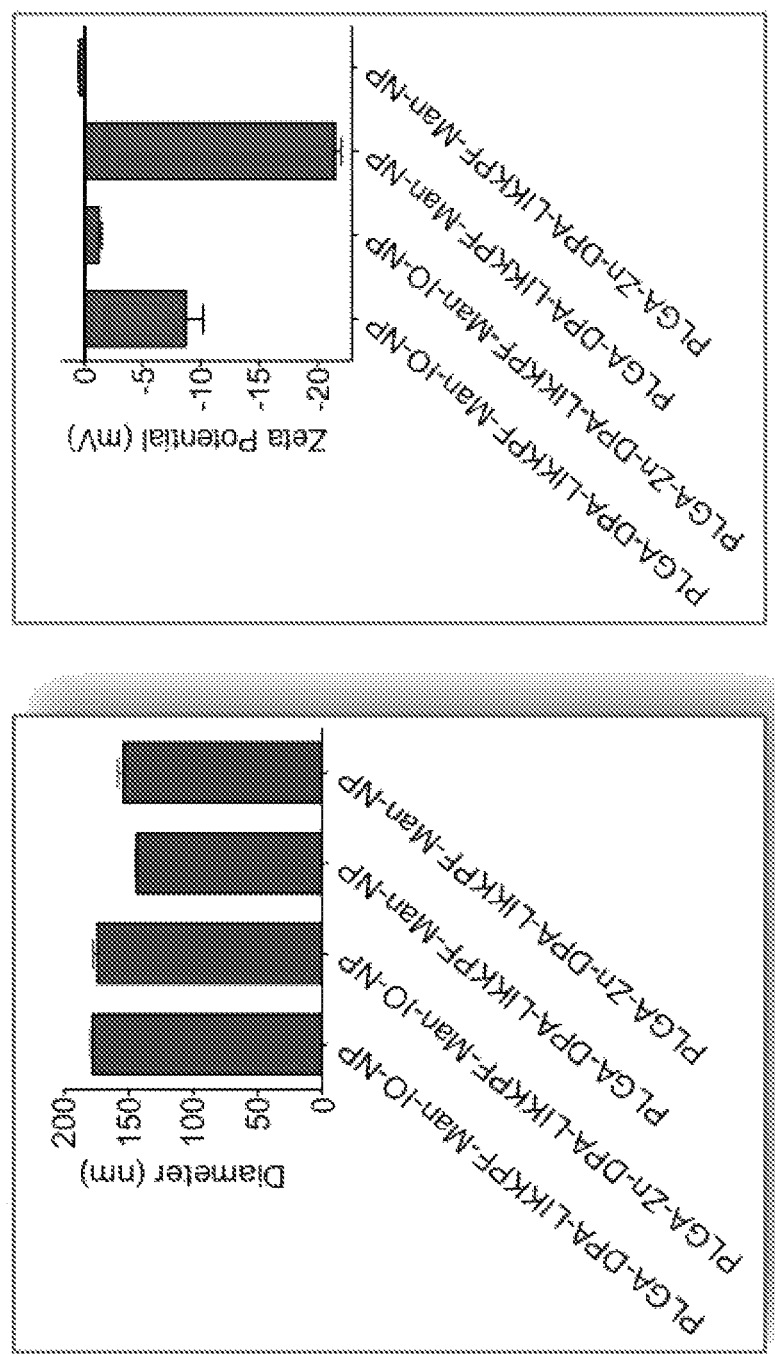
FIG. 4 presents bar graphs showing the size (left panel) and zeta potential (right panel) of various nanoparticles formed as described herein.

FIG. 3 shows TEM images of certain nanoparticles (as indicated above figure). As shown in FIG. 3, the resulting nanoparticles vary in size range but not to a substantial degree. In FIG. 4, the size (left panel) and zeta potential (right panel) of various nanoparticles (as indicated) are depicted.

Example 7

Specificity of Nanoparticles for PS

Figure 5:
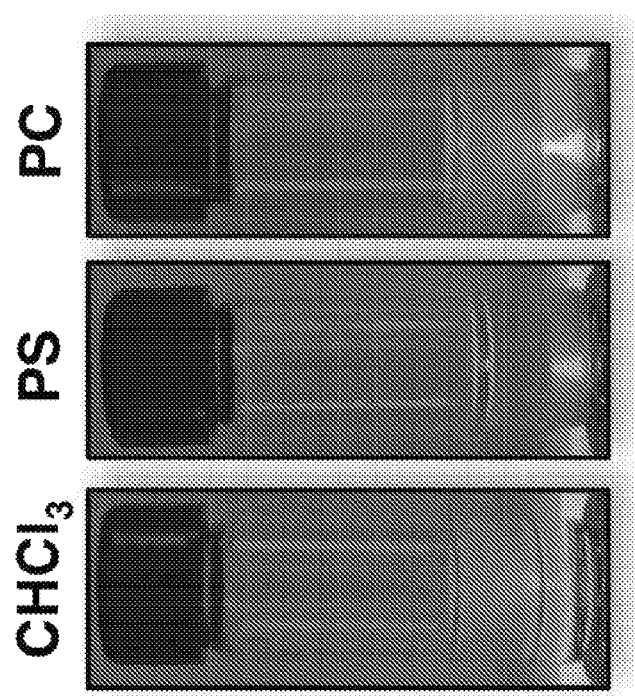
FIG. 5 presents images of vials containing chloroform (CHCl$_3$), phosphatidyl serine (PS) or phosphatidyl choline (PC) in which fluorescent-labeled PS targeting nanoparticles were introduced.

To test the preferential binding ability of the nanoparticle prepared according to Example 5 to PS over other phospholipids viz. phosphatidylcholines (PC), we mixed a suspension of QD-encapsulated blended NPs containing both the Zn2+-DPA binding site and LIKKPF in 10 mM HEPES buffer with either PC or PS in $CHCl_3$. As shown in FIG. 5, in the case of PC in $CHCl_3$, the pink color representing NPs remained in the buffer (upper) layer. With PS in $CHCl_3$, NPs moved to the $CHCl_3$ (lower) layer. This preliminary experiment supports that the NP constructs described herein can distinguish phospholipid solutions of PS over PC

Example 8

Fluorescence of Apoptotic Macrophages

Figure 6:
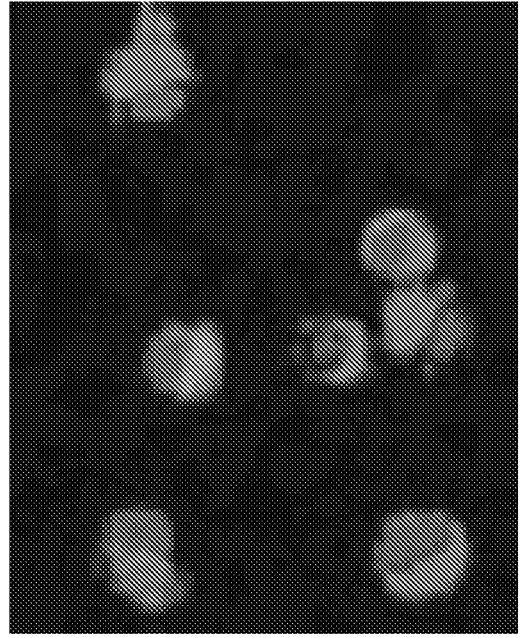
FIG. 6 presents confocal fluorescent micrographs of apoptotic cells incubated with PS targeting fluorescent-labeled nanoparticles.
Figure 6:
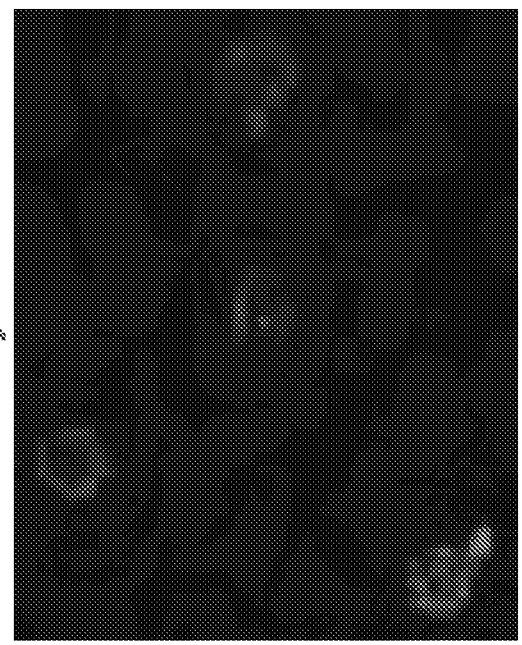

Fluorescence (FL) imaging of QD-encapsulated blended NPs containing both LIKKPF and $Zn^{2+}$-DPA on the surface prepared according to Example 5 was performed. During this procedure RAW 264.7 macrophages were first treated with an apoptotic stimulus, etoposide (50 nM) for 3 h and subsequently incubated with NPs for 10 min at room temperature. This FL imaging shows that the targeted NPs stain the surface of the apoptotic cells demonstrating PS binding on the cell surface, whereas the NPs without any $Zn^{2+}$ binding site shows non-specific uptake (FIG. 6). These results are believed to be due to the fact that $Zn^{2+}$-DPA provides covalent binding to phosphate groups of PS, which LIKKPF provides only non-covalent bonds.

Example 9

MRI of Apoptotic Macrophages

Figure 7:
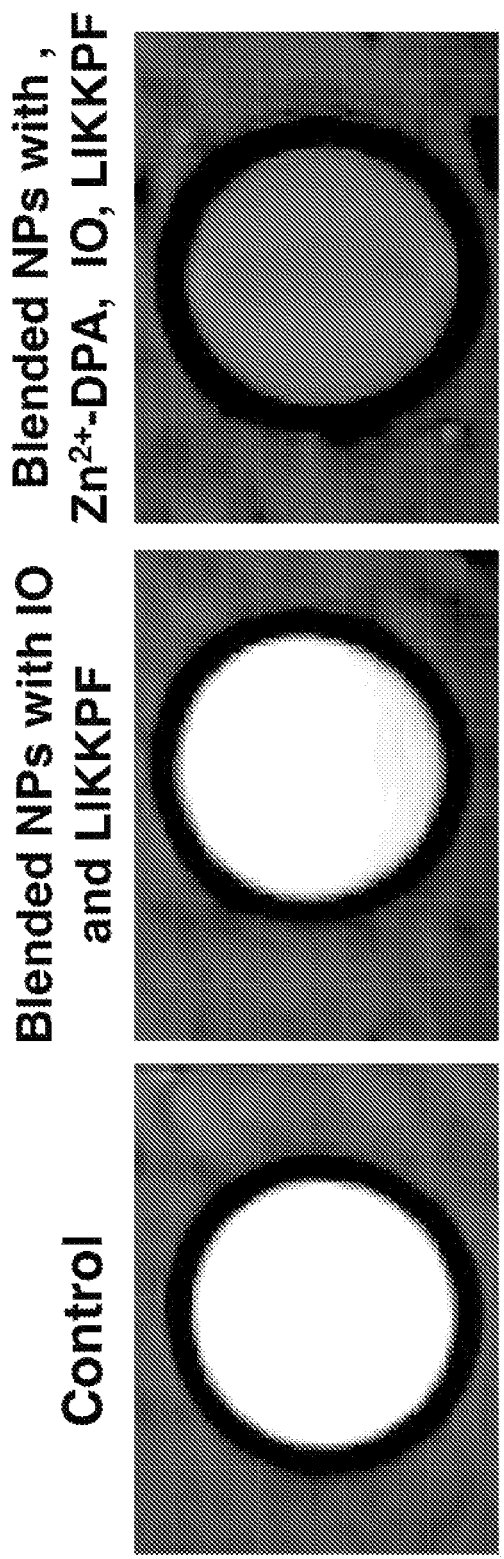
FIG. 7 presents MRI images of apoptotic cells incubated with iron-oxide containing PS targeting nanoparticles.

MRI of apoptotic cell pellets was initiated using IO-encapsulated blended NPs containing both LIKKPF and Zn2+-DPA on the surface (prepared according to Example 5). T2 weighted fast spin echo imaging of loosely packed pellets of mouse RAW 264.7 cells at 7 T was carried out. Apoptosis was induced following the same procedure mentioned above in Example 8. Preliminary imaging showed that the signal intensity of apoptotic cells was drastically lowered after incubation with Zn2+-DPA-NP construct compared with cells that were left untreated or incubated with NPs without Zn2+-DPA (FIG. 7).

Example 10

Synthesis of DSPE-PEG-TPP

Briefly, DSPE-PEG-NH$_2$ was coupled to TPP-(CH$_2$)$_4$-TPP by using EDC/NHS coupling, the product was lyophilized against water for purification and characterized by NMR, MALDI.

Example 11

Assembly of Mitochondrial-Targeting Nanoparticles

Targeted hybrid NPs were prepared via self-assembly of PLGA, PLGA-b-PEG-QD, cholesteryl oleate, DSPE-PEG-TPP, DSPE-PEG-lactobionic acid, and apoA-1 peptide through a double-step modified nanoprecipitation method. PLGA, PLGA-PEG-QD, cholesteryl oleate were mixed. DSPE-PEG-TPP and DSPE-PEG-lactobionic acid were dissolved in 4 wt % ethanol aqueous solution. The lipid solution was heated to 65° C. to ensure all lipids are in the non assembled state. The PLGA-cholesterol solution was added into the preheated lipid solution drop wise under gentle stirring. The mixed solution was vortexed vigorously for 3 min followed by gentle stirring for 2 h at room temperature. The remaining organic solvent and free molecules were removed by washing the NP solution three times using an Amicon Ultra-4 centrifugal filter with a molecular weight cutoff of 10000 Da. To prepare non targeted NPs, PVA was used instead of DSPE-PEG-TPP during the nanoprecipitation process. The resultant NPs were incubated with mimic apoA-1 peptide with an amino acid sequence of FAEKFKEAVKDYFAKFWD at 4° C. for 14 h and was further purified using ultracentrifugation. NP size (diameter, m), polydispersity index (PDI), and surface charge (zeta potential, mV) were obtained from three repeat measurements by dynamic light scattering (DLS) with a Zetasizer Nano-ZS dynamic light scattering detector. QD loading in the NPs was quantified by inductively coupled plasma mass spectrometry (ICP-MS) and apoA-1 loading was determined by following tryptophan absorbance at 280 nm.

Example 12

Characterization of Mitochondrial-Targeting Nanoparticles

Figure 8:
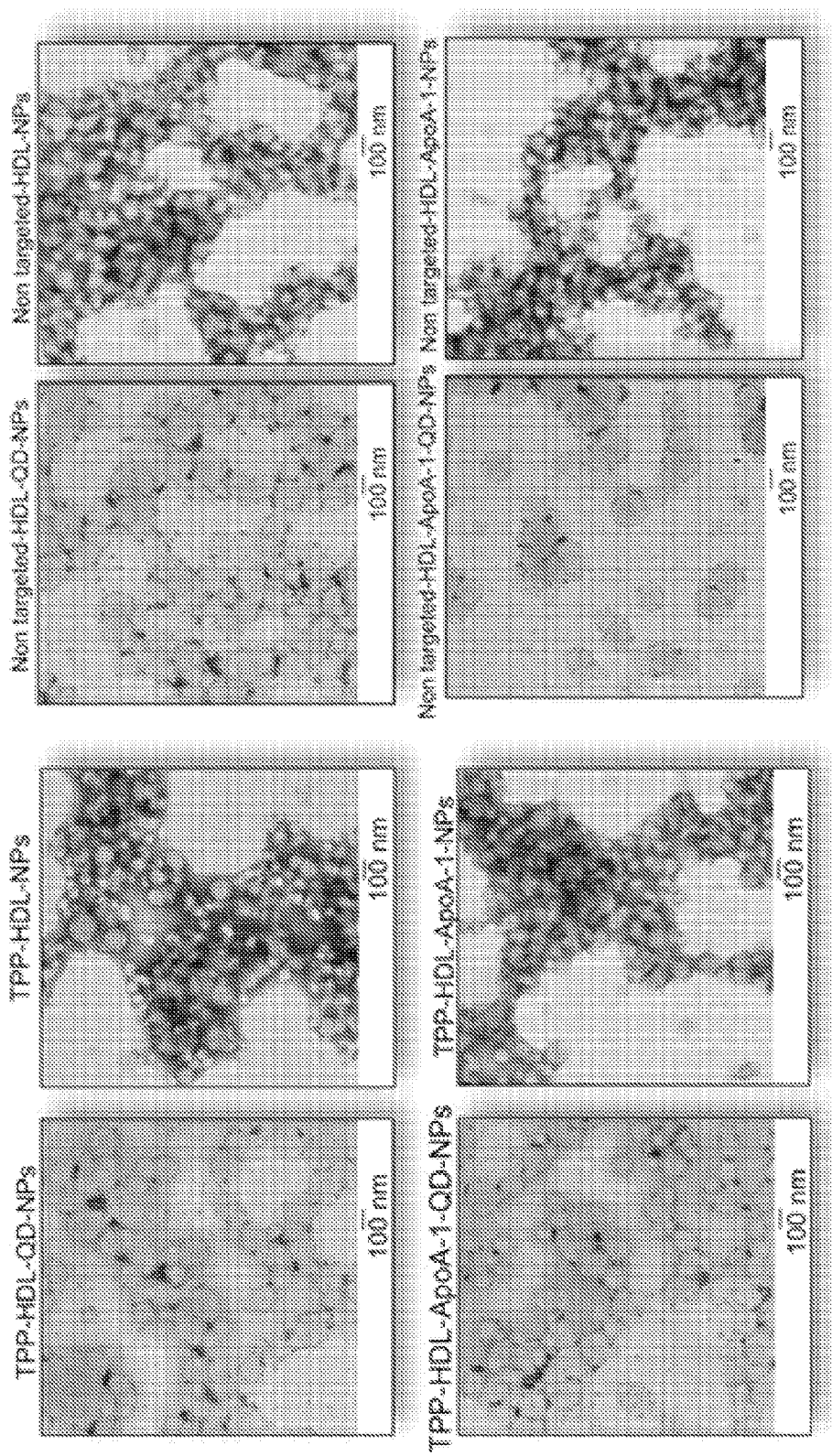
FIG. 8 presents TEM images of mitochondrial matrix targeted nanoparticles.

Transmission electron microscopy (TEM) was used to determine particle size of the nanoparticles resulting from Example 11. FIG. 8 shows the results of the TEM, indicating that the particles are of an appropriate size for mitochondrial uptake.

Figure 9:
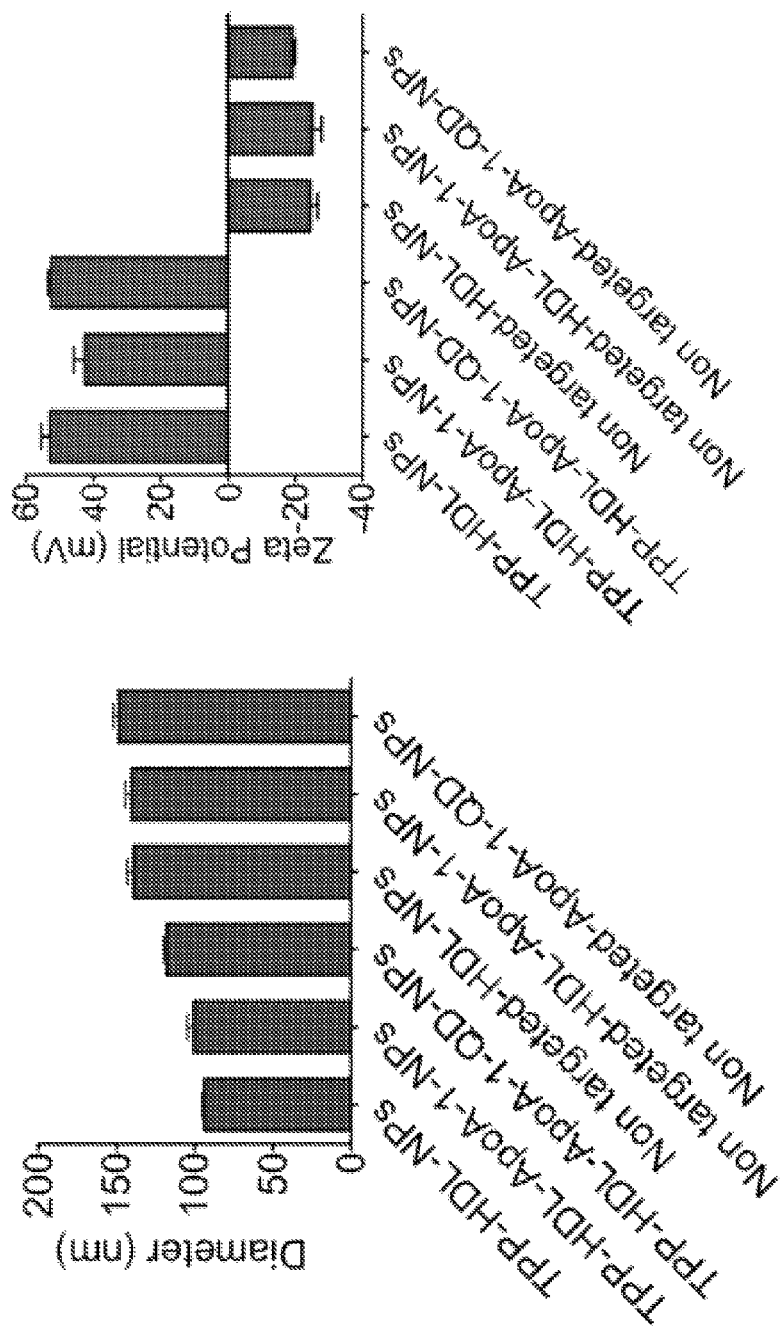
FIG. 9 presents bar graphs showing the size (left panel) and zeta potential (right panel) of the mitochondrial matrix targeted nanoparticles.

The size and zeta potential of the nanoparticles were evaluated as described above in Example 6. The results are presented in FIG. 9, with the size being shown in the left panel and the zeta potential being shown in the right panel.

Figure 10:
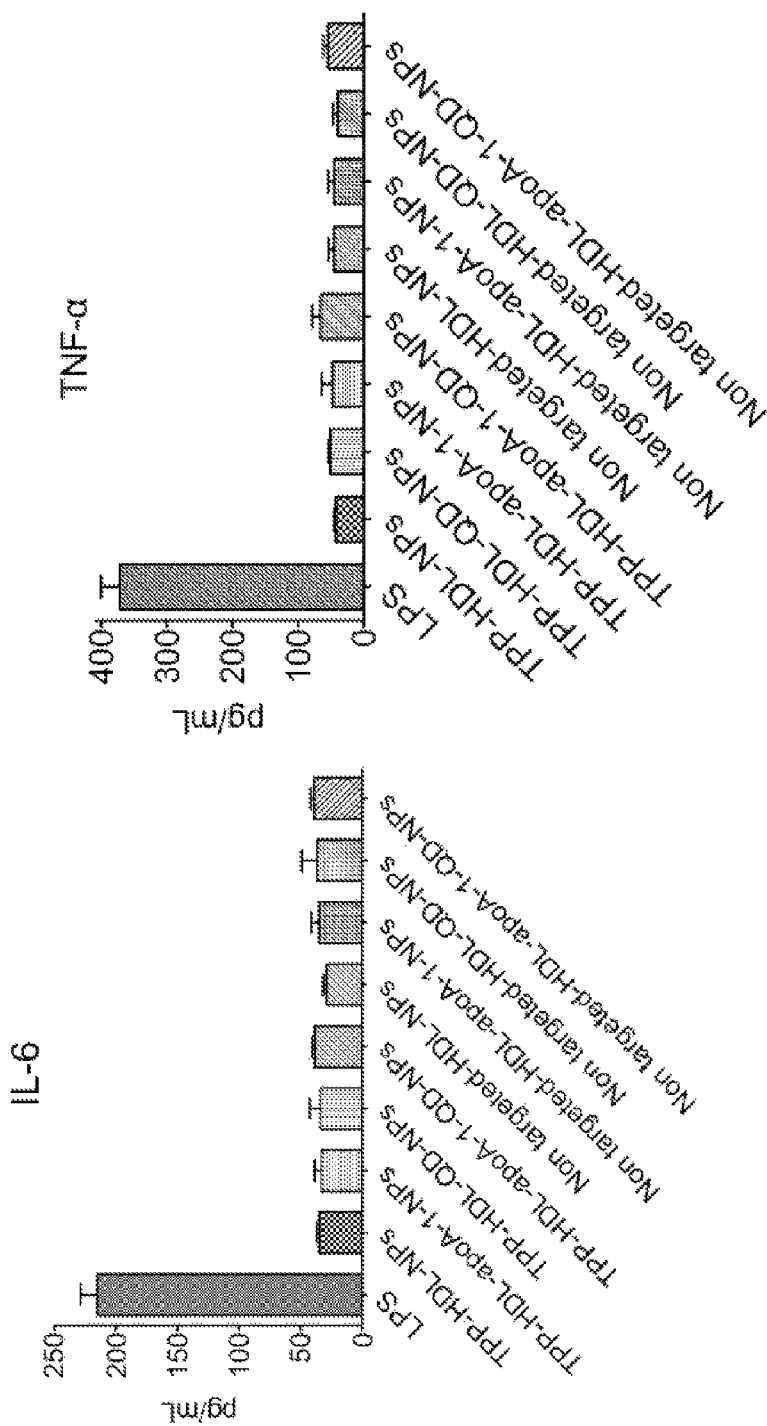
FIG. 10 presents bar graphs showing the results of ELISA assays performed against IL-6 (left panel) and TNF-α (right panel) of macrophages challenged with mitochondria targeted nanoparticles, as indicated.

ELISA analysis was used to determine whether the nanoparticles induced immune activation. RAW macrophages were plated at a density of 2,000 cells/well and grown overnight. Cells were treated with NPs (0.5 mg/mL) and incubated for 12 h. As controls, untreated RAW cells and treatment with 0.125 mg/mL of LPS was carried out. An ELISA assay was performed against the cytokines IL-6 and TNF-α according to the manufacture's protocol. Briefly, the cell lysate was incubated in antibody-coated plates for 2 h at RT, incubated with the cytokine-biotin conjugate and streptavidin working solution. The stabilized chromagen was added to each well followed by a stop solution and the absorbance was recorded at 450 nm. As shown in FIG. 10, the nanoparticles did not induce immune activation.

Example 13

Mitochondrial Uptake of Mitochondrial-Targeting Nanoparticles

Figure 11A:
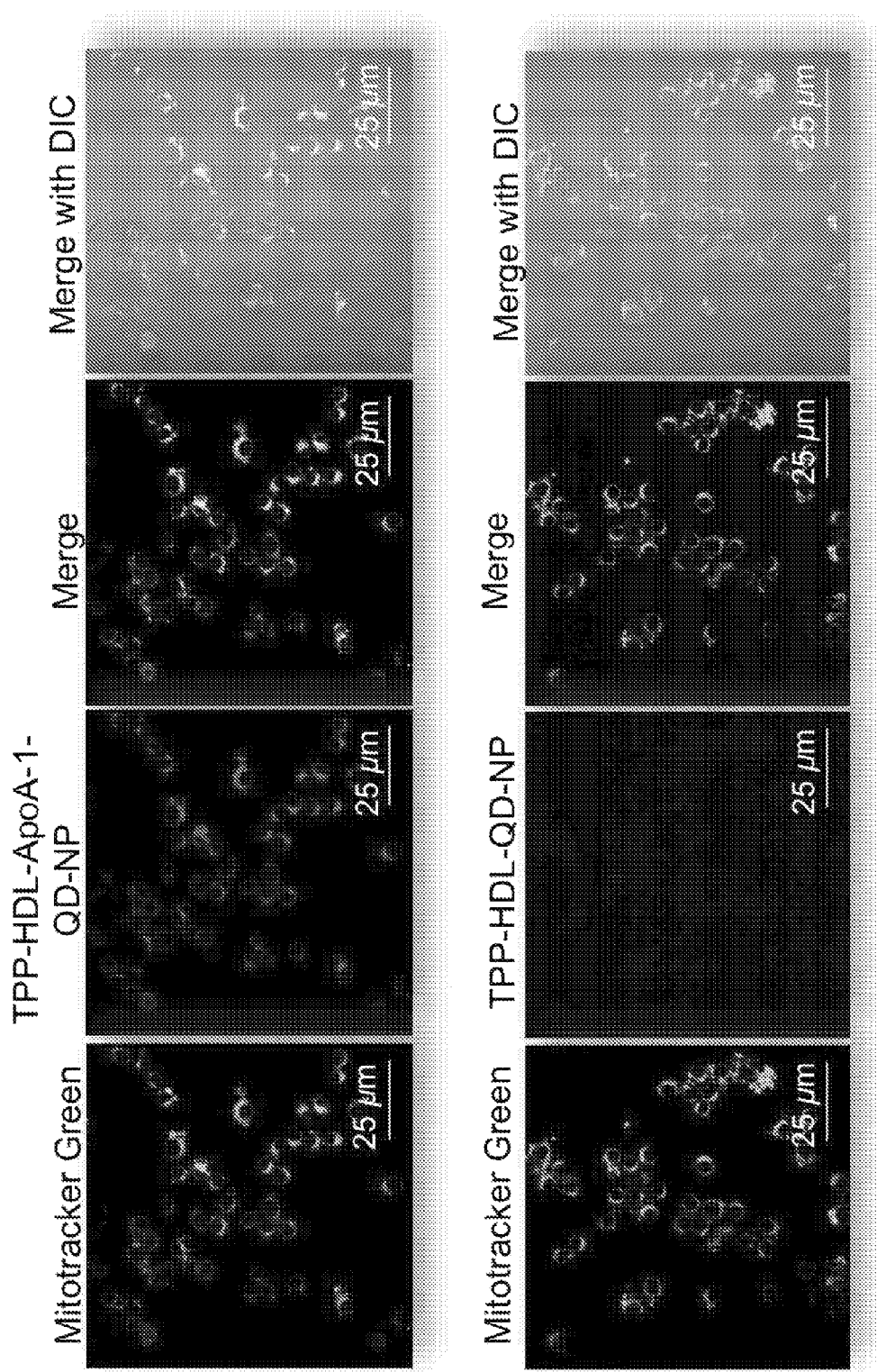
FIGS. 11A-B are confocal images of cells incubated with mitochondrial matrix targeted nanoparticles (A) and with non-mitochondrial targeted nanoparticles (B).
Figure 11B:
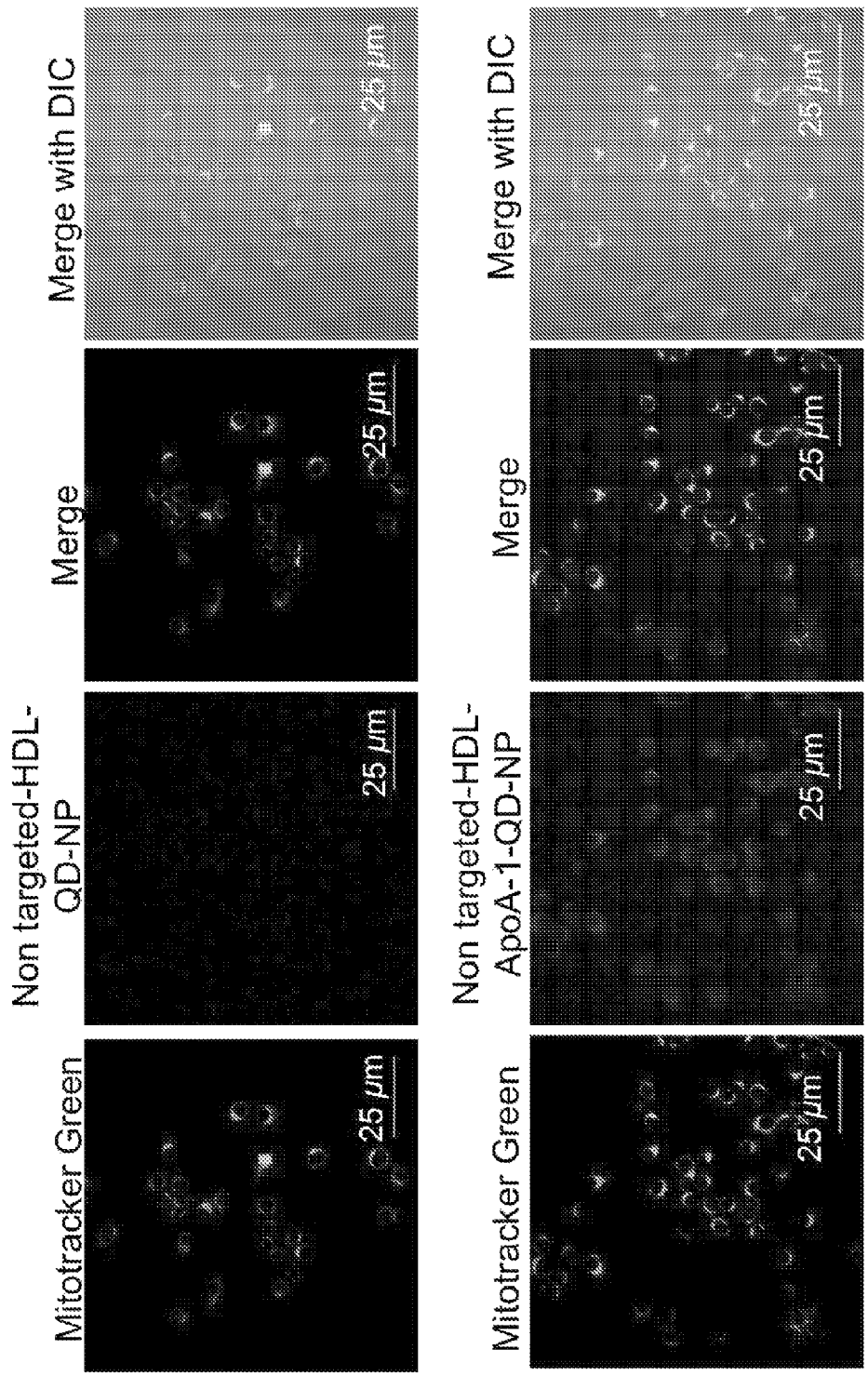

Confocal Fluorescence microscopy was used to determine whether the nanoparticles (prepared according to Example 10) were targeted to mitochondria. RAW and MSC cells were seeded on microscope coverslips (1.0 cm) at a density of $6 \times 10^7$ cells/mL and grown overnight in DMEM. The medium was changed and fluorescent targeted and non-targeted NPs were added to a final fluorophore concentration of 10 µM. The cells were incubated for 4 h at 37° C. in 5% CO$_2$. MitoTracker Green (100 nM) was added and incubated for 45 min at 37° C. The medium was removed and the cells were fixed using cold methanol for 30 min. The coverslips were then rinsed with PBS (3×), water (5×), and mounted on slides using mounting media. Images were collected at xx ms for the FITC and Cy5 channels (FIGS. 11A-B). As shown in FIG. 11A, mitochondrial matrix targeted nanoparticles preferentially accumulate in mitochondria. While non-targeted nanoparticles accumulate in the cytosol (FIG. 11B).

Example 14

Cholesterol Binding Experiments

Figure 12:
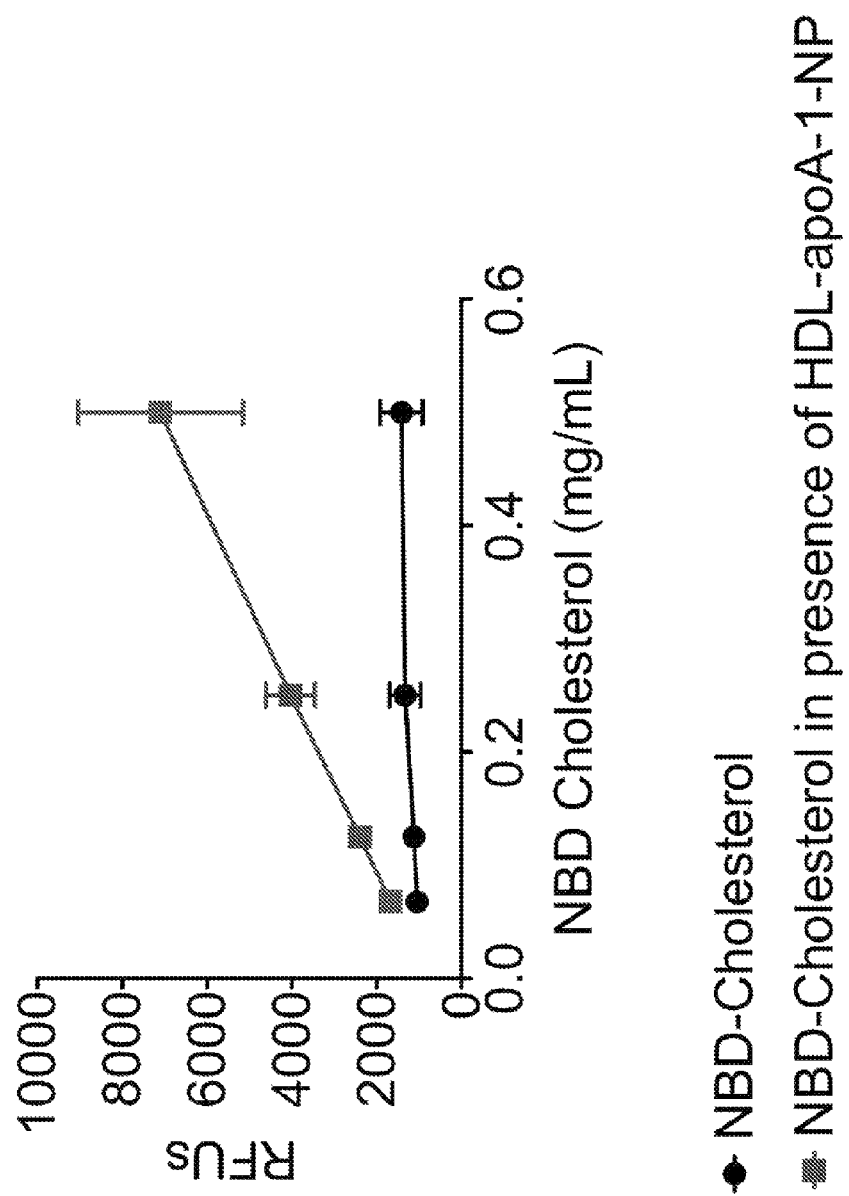
FIG. 12 is a graph showing cholesterol binding effects of a HDL-mimicking nanoparticle as described herein.

A fluorescent sterol, NBD-cholesterol, 22-(N-7-nitrobenz-2-oxa-1,3-diazo-4-yl)-amino-23,24-bisnor-5-cholen-3β-ol)) was used to examine the HDL-mimicking NP mediated cholesterol uptake to explore the therapeutic potential. The weak fluorescence of NBD-cholesterol in polar environment was enhanced by the presence of non-polar HDL-NP matrix (FIG. xx). This preliminary experiment is indicative that cholesterol can irreversibly bind to TPP-HDL-apoA-1-NPs and this platform can participate in reverse cholesterol transport pathway for providing therapeutic effects. Cholesterol binding to HDL-apoA-1-NPs was determined by adding 5 µL of varying concentrations of NBD-cholesterol in DMF to 5 mg/mL of 995 µL of HDL-apoA-1-NPs in water. The solutions were vortexed and incubated for ~20 min. Fluorescence of the solutions were followed by exciting at 473 nm and emission from 500 to 600 nm. The binding of NBD-cholesterol to HDL-apoA-1-NPs leads to an increase in fluorescence intensity (FIG. 12).

Example 15

Cytotoxic Properties of Mitochondria Targeted NPs

Figure 13:
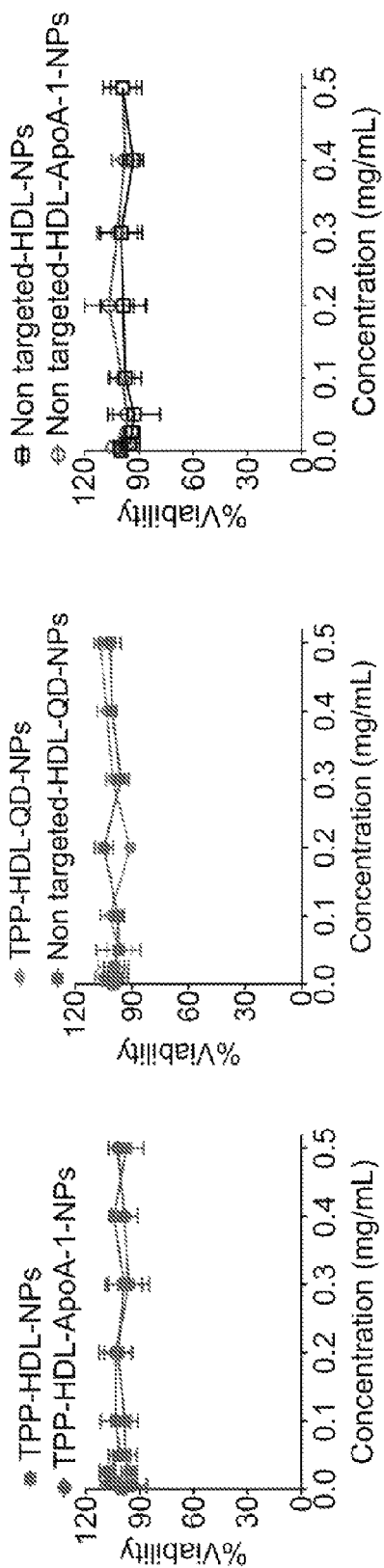
FIG. 13 presents graphs showing results of cytotoxicity experiments of HDL-mimicking nanoparticles, as indicated.

The cytotoxic behavior of all the NPs was evaluated using the MTT assay against RAW and MSC cells. Cells (2000 cells/well) were seeded on a 96-well plate in 200 µL of DMEM medium for RAW cells and xx medium for MSC cells and incubated for 24 h. The cells were treated with targeted and non-targeted NPs at varying concentrations (with respect to PLGA) and incubated for 12 h at 37° C. The medium was changed, and the cells were incubated for additional 60 h. The cells were then treated with 20 μL of MTT (5 mg/mL in PBS) for 5 h. The medium was removed, the cells were lysed with 100 μL of DMSO, and the absorbance of the purple formazan was recorded at 550 nm. Each well was performed in triplicate. All experiments were repeated three times. Cytotoxicity data were plotted with Graph Pad Prism (San Diego, U.S.A) (FIG. 13).

Thus, embodiments of APOPTOSIS-TARGETING NANOPARTICLES are disclosed. One skilled in the art will appreciate that the nanoparticles and methods described herein can be practiced with embodiments other than those disclosed. The disclosed embodiments are presented for purposes of illustration and not limitation.

What is claimed is:

1. A nanoparticle comprising:
cholesteryl oleate
a polymer consisting essentially of poly(lactic-co-glycolic acid) (PLGA);
a block copolymer comprising a PLGA block and a polyethylene glycol (PEG) block;
a first compound comprising PEG attached to a phospholipid, and a targeting moiety attached to the PEG or conjugated to a lipid moiety for interaction with the phospholipid, wherein the targeting moiety is selected from the group consisting of a zinc 2,2'-dipicolylamine ($Zn^{2+}$- DPA) coordination complex, a PS-targeting polypeptide comprising an amino acid sequence selected from the group consisting of LIKKPF (SEQ ID NO:1), PGDLSR (SEQ ID NO:2), and DAHSFS (SEQ ID NO:3), a triphenyl phosophonium (TPP) moiety, a Szeto-Shiller peptide, and a rhodamine cation;
a second compound comprising a macrophage targeting moiety attached to a phospholipid, wherein the macrophage targeting moiety is selected from the group consisting of a mannose moiety, a galactose moiety, or lactobionic acid moiety; and
an apoA-I peptide mimetic,
wherein the polymer consisting essentially of PLGA and the PLGA block of the block copolymer form a hydrophobic core of the nanoparticle,
wherein the PEG block of the block copolymer forms a hydrophilic layer surrounding the core,
wherein the cholesterol oleate is bound to the core,
wherein the apoA-I peptide mimetic is bound to the core,
wherein the targeting moiety extends from the core, and
wherein the macrophage targeting moiety extends from the core.

2. A nanoparticle according to claim 1, wherein the phospholipid of the first and second compounds comprises distearoyl-snglycero-3-phosphoethanolamine.

3. A nanoparticle targeting apoptotic cells or products indicative of apoptotic cells, the nanoparticle having a diameter from 20 nanometers to 300 nanometers and comprising:
cholesteryl oleate
a polymeric core;
a layer comprising polyethylene glycol (PEG) surrounding the core;
a phospholipid monolayer between the core and the layer comprising PEG;
a first targeting moiety bound to the nanoparticle, wherein the first targeting moiety comprises a phosphatidylserine (PS) targeting moiety or a mitochondria matrix targeting moiety, wherein the first targeting moiety is selected from the group consisting of a zinc 2,2'-dipicolylamine (Zn2+- DP A) coordination complex and a phosphatidylserine-targeting polypeptide comprising an amino acid sequence selected from the group consisting of LIKKPF (SEQ ID NO:1), PGDLSR (SEQ ID NO:2), and DAHSFS (SEQ ID NO:3); and
a therapeutic agent releasable from the nanoparticle, wherein the therapeutic agent is for treating vascular plaques, atherothrombotic vascular disease or coronary heart disease.

4. A nanoparticle according to claim 3, wherein the first targeting moiety selectively binds to PS.

5. A nanoparticle according to claim 3, further comprising an apoA-1 peptide mimetic.

6. A nanoparticle according to claim 3, further comprising a therapeutic agent selected from the group consisting of one or more statin, one or more fibrate, and combinations thereof.

7. A nanoparticle according to claim 3, further comprising a PCSK9 repressor.

8. A nanoparticle according to claim 3, further comprising chenodeoxylcholic acid.

9. A nanoparticle according to claim 3, further comprising a macrophage targeting moiety.

10. A nanoparticle according to claim 7, wherein the macrophage targeting moiety comprises mannose, galactose, or lactobionic acid.

* * * * *

UNITED STATES PATENT AND TRADEMARK OFFICE
CERTIFICATE OF CORRECTION

PATENT NO. : 9,901,616 B2
APPLICATION NO. : 14/240081
DATED : February 27, 2018
INVENTOR(S) : Dhar et al.

Page 1 of 1

It is certified that error appears in the above-identified patent and that said Letters Patent is hereby corrected as shown below:

Column 16, Line 60, delete Scheme. Insert therefore:

-- , Scheme II --

Signed and Sealed this
Fourth Day of December, 2018

Andrei Iancu
*Director of the United States Patent and Trademark Office*